US006323189B1

(12) United States Patent
Hardinge-Lyme

(10) Patent No.: US 6,323,189 B1
(45) Date of Patent: Nov. 27, 2001

(54) CHITOSAN-CONTAINING LIQUID COMPOSITIONS AND METHODS FOR THEIR PREPARATION AND USE

(75) Inventor: Nicholas Hardinge-Lyme, Palm Beach, FL (US)

(73) Assignee: e-nutriceuticals, Inc., New York, NY (US)

( * ) Notice: Subject to any disclaimer, the term of this patent is extended or adjusted under 35 U.S.C. 154(b) by 0 days.

(21) Appl. No.: 09/362,672

(22) Filed: Jul. 29, 1999

Related U.S. Application Data

(60) Provisional application No. 60/094,679, filed on Jul. 30, 1998, provisional application No. 60/124,788, filed on Mar. 17, 1999, and provisional application No. 60/141,021, filed on Jun. 25, 1999.

(51) Int. Cl.⁷ .......................... A61K 31/722; C08B 37/08
(52) U.S. Cl. ................................ 514/55; 536/20
(58) Field of Search ................... 536/20; 514/55

(56) References Cited

U.S. PATENT DOCUMENTS

| | | | |
|---|---|---|---|
| 4,202,881 | 5/1980 | Gross et al. | 424/70 |
| 4,223,023 | 9/1980 | Furda | 424/180 |
| 4,363,801 | 12/1982 | Nagyvary | 424/180 |
| 4,474,769 | 10/1984 | Smith | 424/180 |
| 4,512,968 | 4/1985 | Komiyama et al. | 424/48 |
| 4,938,998 * | 7/1990 | Stock | 427/223 |
| 5,453,282 | 9/1995 | Kanauchi et al. | 424/464 |
| 5,599,916 * | 2/1997 | Dutkiewicz et al. | 536/20 |
| 5,654,001 | 8/1997 | Kanauchi et al. | 424/464 |
| 5,736,532 | 4/1998 | Furda | 514/55 |
| 5,773,608 | 6/1998 | Yen et al. | 536/124 |

FOREIGN PATENT DOCUMENTS

| | | |
|---|---|---|
| WO 91/00298 | 1/1991 | (WO) . |
| WO 98/32335 | 7/1998 | (WO) . |
| WO 98/34625 | 8/1998 | (WO) . |

OTHER PUBLICATIONS

Nauss et al., (1983), *Lipids*, vol. 18, No. 10, pp. 714–719.
Muzzarelli R.A.A. (1996), "Chitsan–Based Dietary Foods", *Carbohydrate Polymers*, vol. 29, No. 4, pp. 309–316.
Patent Abstracts of Japan (Sep. 5, 1984), "Chitosan Suspension and its Production", vol. 008, No.193.

* cited by examiner

*Primary Examiner*—Kathleen Kahler Fonda
(74) *Attorney, Agent, or Firm*—McDonnell Boehnen Hulbert & Berghoff

(57) ABSTRACT

The invention is novel liquid chitosan-containing compositions, their methods of preparation, and their methods of use. In particular, the invention is a novel chitosan-containing liquid suspension composition which remains stable and is usable as an additive, for instance, in water or aqueous solution (i.e., water-based liquids).

44 Claims, No Drawings

CHITOSAN-CONTAINING LIQUID
COMPOSITIONS AND METHODS FOR
THEIR PREPARATION AND USE

This application claims priority under 35 U.S.C. 119(e) to the following provisional U.S. application Ser. No. 60/094,679 filed Jul. 30, 1998, 60/124,788 filed Mar. 17, 1999, and 60/141,021 filed Jun. 25, 1999.

TECHNICAL FIELD OF THE INVENTION

The present invention pertains to novel chitosan-containing liquid compositions, their methods of preparation, and their methods of use. In particular, the invention pertains to a chitosan-containing liquid suspension composition which remains stable and is usable as an additive, for instance, in water or water-based liquids.

BACKGROUND OF THE INVENTION

We live in a society obsessed with overall personal appearance and losing weight. Despite this obsession, medical reports confirm that 68% of all Americans are overweight, and 33% of those past the age of 20 are clinically obese. This equates to 64 million overweight adults in the just the United States alone. Beyond the obvious cosmetic considerations, obesity is one of the leading causes of heart disease, hypertension, stroke, and diabetes, and is a contributing cause in cancer. The size of the market for weight control products is estimated at over $100 billion per annum worldwide and is ever increasing. There clearly is a need for an effective, safe, and palatable weight control product to stop this growing problem.

The medical profession has long proclaimed the benefits of a high fiber, low fat diet. Chitosan has received considerable attention in this context since it can be applied to bind fat in food, creating an indigestible mass that lets the fat pass unabsorbed through an individual's digestive system and right out of the body. Chitosan (i.e., (1→4) 2-amino-2-deoxy-β-D-glucosamine, also known as polyglucosamine) is a water-immiscible biopolymeric compound comprising partially or fully deacetylated chitin. Chitin is a cellulose-like polymer that is present in fugal walls and the exoskeletons of arthropods, including insects, crabs, shrimp, and lobsters. Chitosan can bind up to 4 to 6 times its weight in oils, greases, and toxic substances (Nauss et al., Lipids, 18 (10), 714–719 (1983)). This capacity of chitosan derives from its possession of positively charged amino groups that bind to negatively charged fatty acids (the building blocks of fat) and bile acids (used in making cholesterol).

Chitosan's unique abilities are responsible for its employ as an additive or primary component in numerous applications in the fields of food, health, cosmetics, agriculture, waste-water treatment, as well as in other industries. In the food and health industry, chitosan currently is available in tablet form under several brand names. Also, tablets containing chitosan combined with ascorbic acid are presently marketed. Ascorbic acid acts in synergy with chitosan to provide fat absorption properties which are greatly enhanced over those of chitosan alone. However, chitosan tablets are bulky, need to be taken in large quantities, have an unpleasant taste, and may possess other noticeable side effects. Thus, there is a current need for a product that provides for weight control and is easy to use, particularly in comparison to capsules containing chitosan.

"U.S. Pat. No. 5,736,532 pertains to a fat absorption and cholesterol reduction formulation comprising chitosan and nicotinic acid, and describes the use of this formulation to reduce cholesterol. The patent describes that the formulation must contain chitosan and nicotinic acid, and additionally can contain one or more other water-soluble vitamin acid, such as ascorbic acid, folic acid, etc. The patent describes the formulation of the mixture as a powder which is then formed into tablets or packed into gelatin capsules. Of course, these tablers and capsules are as inconvenient to take as are the chitosan tablets. Also, it is well known that oral nicotinic acid (niacin) taken by itself in high doses is effective at reducing serum cholesterol and triglycenide levels. However, in therapeutic doses, niacin can have several side effects, including flushing, skin rash, liver problems, activation of peptic ulcers, gout, worsening of diabetes control, as well as others."

Certain patents disclose, among other things, chitosan that may be in a liquid formulation. The related U.S. Pat. Nos. 5,453,282, and 5,654,001 each describe a liquid chitosan formulation that contains ascorbic acid (see, e.g., Table 8 disclosing a formulation containing fruit juice (210 g/l), sugar (100 g/l), ascorbic acid (1 g/l), essence (1 g/1), and chitosan (20 g/1)) that can be used in treating obesity. However, the liquid chitosan formulation of these patents has a questionable shelf life in that the liquid contains high amounts of sugar and no preservatives. Moreover, the patents provide no teaching of ways to solubilize the chitosan in the liquid (i.e., the weight ratio of chitosan to ascorbic acid employed in Table 8 is 20:1, and no instructions are given in the patent regarding special mixing to dissolve the chitosan in the liquid), meaning the chitosan in the disclosed liquid composition likely remains in flake or powder form.

Similarly, U.S. Pat. No. 4,223,023 claims a "method of reducing lipid absorption in mammals which comprises orally administering to the mammal an amount of chitosan effective to substantially reduce the lipid absorption" (claim 1). Example 6 of this patent pertains to a chitosan powder mixture for oral administration which contains chitosan (80 g), lactose (10 g), sucrose (9.9 g), and flavor. The powder mixture is to be administered as a suspension in water, or other liquid. However, the patent provides no instruction regarding how much liquid the powder is to be added to, much less provide any instruction regarding solubilizing the chitosan in the liquid. All the remaining Examples of this patent pertain to formulations in which the chitosan is combined in the mixture with either shortening or fatty acid. Such combination will cause the precipitation of the chitosan in the composition within a short period of time.

By comparison, U.S. Pat. Nos. 4,202,881, 4,363,801, 4,474,769, and 4,512,968, and PCT International Application WO 98/32335 describe: (a) treatment of chitosan with acid, (b) rendering chitosan water-soluble by treatment with acid, and/or (c) chitosan liquid formulations. Namely, U.S. Pat. No. 4,202,881 claims a process for shampooing and conditioning hair that comprises adding to hair an aqueous solution, emulsion, or gel containing a "water soluble salt of chitosan, said chitosan salt having been prepared by reacting chitosan . . . with a sufficient amount of acid to neutralize the free amino groups present in said chitosan and to form a water soluble salt thereof" (claim 1). Col. 2., lines 23–43 describes that amino groups in chitosan can be neutralized with acids (especially with acetic acid, formic acid, and lactic acid) to obtain salts which are water soluble. The patent, however, fails to describe the process by which a chitosan-containing solution, emulsion, or gel can be obtained without adding the water-soluble salt of a chitosan to hair conditioner and/or hair shampoo.

U.S. Pat. No. 4,512,968 claims a chitosan-containing composition (including a liquid mouth rinse) for reducing dental caries (claim 1). Example 4 describes an aqueous mouth rinse formulation and Example 6 describes a liquid oral freshener. Col. 2, lines 37–47 describes that chitosan is first dissolved in inorganic weak acids to render it water-soluble. The patent, however, fails to describe the process by which a chitosan-containing composition can be obtained without including in the formulation other ingredients that impact the character of the composition (e.g., ethyl alcohol, sodium lauryl sulfonate, sodium α-olefinsulfonate, sodium lauroyl sarcosinate, and/or glycerine or other agents).

By comparison, U.S. Pat. No. 4,474,769 claims a chitosan formulation as a contraceptive. Col. 2, lines 44–53 describes that chitosan is first dissolved in weak acids (especially acetic acid, formic acid, and lactic acid). The chitosan amount can range from 10 ppm to 5%, and the amount of acidic material used to dissolve the chitosan can range from 5 ppm to 10%.

U.S. Pat. No. 4,363,801 claims a "method of treating hyperbilirubinemia which comprises orally administering to the affected patient an amount of soluble chitosan effective to substantially reduce the amount of bilirubin in the blood" (claim 1). Col. 3., lines 11–18 describes that chitosan is first dissolved in weak acids (especially acetic acid, formic acid, and citric acid) to produce a chitosan salt. The chitosan salt preferably is formed by dissolving chitosan in the weak acid, agitating the solution (e.g., in a blender), lyophilizing the solution, and pulverizing the chitosan salts produced by the lyophilization to obtain a finely ground powder. The ground powder then is mixed when ready to use with a solution of water, or other beverage.

Similarly, PCT International Application WO 98/32335 claims a chitosan solution for treating cotyledonous plants. The paragraph bridging pages 15 and 16 describes preparation of an aqueous chitosan acetate solution which exhibits sufficient longevity to be packaged in a laboratory and transported for use in the field. This solution is obtained by vigorously stirring chitosan flakes in water at a temperature of 60° C., adding acetic acid with continued stirring at elevated temperature to dissolve the chitosan, filtering the solution, diluting with water, and packaging the solution.

Thus, these references disclose at most a liquid composition produced by treatment of chitosan with acid. It is not clear whether these preparations all contain chitosan in solubilized form and/or exhibit any stability. More important, since certain of these preparations contain other ingredients specific for particularized uses, its not clear whether these preparations are appropriate for human consumption in a weight treatment regimen, much less are palatable for human consumption.

Finally, PCT International Application WO 98/34625 pertains to so-called "microcrystalline chitosan" that can be employed for reducing absorption of lipids. The microcrystalline chitosan optionally is in the form of a gel-like dispersion or powder. The microcrystalline chitosan appears to be prepared by a process that involves aggregating the glucosamine macromolecules from a solution of chitosan in an acid by introduction of an alkaline solution (i.e., as described in PCT International Application 91/00298). However, it is not clear from the disclosure exactly what the characteristics of the gel should be (e.g., rigidity, etc.), and what other components optionally can be present in, or are needed for the dispersion.

"More recently, an extracted and highly refined liquid form of polyglucosamine has become available for sale, e.g., FTF Liquid Chitosan (sold by a variety of Internet vendors including Discover Nutrition, also described under the name Maderia Liquid PolyGlucosamine, marketed by Maderia, Inc. This liquid form comprises purified liquid polyglucosamine (i.e., solubilized polyglucosamine) with many of the common components of chitosan removed, that must be measured in precise quantities (e.g., an exact number of drops) into another liquid to form an all-liquid chitosan dosing solution. The product itself is a clear solution. The miscibility of the liquid chitosan in another liquid means there is no clear change in form of the solution containing chitosan as compared to the solution which does not contain chitosan. This causes consumer uncertainty as to whether the beverage being consumed truly is a chitosan-containing solution, and could conceivably lead to overdosing (e.g., as where the chitosan is added to the solution more than once). Moreover, the lack of change of form of the solution denies the consumer any clear sense of satisfaction that a chitosan-containing weight treatment solution is being imbibed. Of course, many times in a weight treatment regimen, the perception that an action is being taken and an effect will be observed as an consequence of that action, is key to obtaining a beneficial result.

Along similar lines, Collaborative Laboratories markets a polyalectrolyte composed of ascorbic acid and polyglucosamine (i.e., Ascorbyl Glucosearine™). This polyelectrolyte is not described as being effective for the prevention of fat absorption (although a substantial number of its properties are described). However, if the polyclectrolyte can be so employed (e.g., in a weight treatment regimen), it suffers from the same problems as described for solubilized chitosan. Namely, the polyglucosamine is a liquid that is water-soluble."

Accordingly, the present invention provides novel chitosan-containing liquid compositions, as well as methods for their preparation and use. The chitosan-containing compositions of the invention are palatable and can be employed, inter alia, in a weight treatment program. In particular, the invention desirably provides a chitosan-containing liquid suspension composition which remains stable and is usable as an additive, for instance, in water or water-based liquids. These and other objects and advantages of the present invention, as well as additional inventive features, will be apparent from the description of the invention provided herein.

BRIEF SUMMARY OF THE INVENTION

The present invention provides, inter alia, novel liquid chitosan-containing compositions, their methods of preparation, and their methods of use. In particular, the invention provides a chitosan-containing liquid suspension composition which remains stable and is usable as an additive, for instance, in water or water-based liquids.

DETAILED DESCRIPTION OF THE PREFERRED EMBODIMENTS

The present invention pertains to novel liquid chitosan-containing compositions, their methods of preparation, and their methods of use. In particular, the invention desirably provides stable chitosan-containing compositions (especially a stable liquid suspension composition). The invention further desirably provides a process for producing the stable chitosan-containing compositions (especially a liquid suspension composition). The invention further provides methods of using the stable chitosan-containing compositions (especially a stable liquid suspension composition), e.g., in a weight treatment program.

The present invention accordingly pertains to products (especially so-called "weight treatment products" defined below) which are described herein by various names, e.g., "chitosan-containing compositions of the invention", "liquid chitosan-containing compositions", "chitosan suspensions", "chitosan liquid suspension compositions", etc., and more particularly, described by the proprietary names, "Kytabsorbe™" and "X-Fat™". A particularly preferred formulation of the invention is that described in Example 5, which further can be modified in terms of the acid employed, flavoring employed, etc. Thus, the invention makes available chitosan in a liquefied form that desirably exhibits an enhanced palatability, effectiveness, and ease of use (e.g., as compared to tablet formulations, and liquid formulations). There are certain improvements accomplished by the products of the invention that make them preferable over other available chitosan products. For instance, the liquid chitosan-containing compositions of the invention are preferable because: (1) the products control fat absorption, optimally resulting in weight treatment; (2) the products are easy to use (e.g., about a half ounce of liquid product is simply poured into a beverage (or consumed "as is") and drunk before, during, or after a meal, and the fat absorption process begins); (3) the products are derived primarily from natural ingredients and optionally contain no stimulants (e.g., caffeine or other agents present in certain other weight loss promoting formulations); (4) the products are sufficiently palatable to encourage subject usage; and (5) optimally, the products exhibit long-term stability (i.e., shelf-life). Further, the chitosan-containing compositions of the invention are favorable in that they desirably do not contain the odious fishy taste and smell of seafood that is inherent in chitosan.

Liquid Chitosan-Containing Compositions

The novel liquid chitosan-containing compositions preferably are stable compositions, and optimally, are stable liquid suspension compositions, and desirably are stable under commercial and industrial applications, as well as consumer use. In particular, the present invention provides a stable liquid suspension composition that desirably comprises (e.g., consists essentially of) chitosan, a non-fatty acid or salt thereof, and water or aqueous solution, wherein each are present in the composition in a stabilizing amount sufficient to effect the formation of a stable liquid suspension.

The term "stable liquid suspension" employed herein refers to, unless otherwise indicated, a chitosan-containing liquid suspension that, after preferably at least about 12 months, desirably after at least about 5 years, and optimally, after at least about 20 years of storage, optimally at about 25° C., remains flowable, and has little or no settlement of solids. The chitosan-containing liquid suspensions according to the invention also desirably are stable (i.e., remain flowable, and have little or no settlement of solids) after being maintained at a temperature from about 0° C. to about 100° C., especially after being maintained at a temperature from about 10° C. to about 50° C., for a period of time ranging from preferably at least about 12 months, desirably at least about 5 years, and optimally, at least about 20 years. It is preferable that the stable liquid suspension according to the invention is stable indefinitely, or nearly indefinitely. It further is desirable according to the invention that the chitosan-containing compositions that are not suspensions exhibit stability as described for the liquid suspension compositions.

A "suspension" as described herein is a two-phase system in which one phase (the dispersed phase, also called the discontinuous or internal phase) is distributed as particles or droplets in a second phase (also called the external phase, continuous phase, or dispersing medium). Suspensions can be made up of particles that are gaseous, liquid, or solid, comprising suspensions which are solid/gas (e.g., aerosol), solid/solid, solid/liquid, liquid/liquid (e.g., emulsions), and gas/liquid (e.g., foams). Desirably according to the invention, the suspension is any chitosan-containing system in which small solid or liquid particles are more or less evenly dispersed in a liquid medium. Optimally the suspension is a liquid/liquid suspension. An especially preferred suspension of the invention has a uniform dispersion of the particles throughout the liquid. Preferably the dispersed particles desirably are of such a size that they do not settle rapidly in the container. Optimally, the surface area of the particles are so much greater than their volume that the particles tend not to settle out by gravity (i.e., they tend to neither sink, nor float). In the event that any small amount (i.e., not significant) sedimentation does occur in a suspension of the invention, the sediment preferably does not form a hard cake, but desirably is capable of re-dispersion with minimal effort.

"A suspension according to the invention preferably is a colloid suspension having a particle size range of from about 1–10 nanometers (10–100 Angstroms) to the size at which the particles become visible in an optical (i.e., light) microscope (about 0.5 to 5 micrometers). Because of their small size, colloidal dispersions undergo little or no sedimentation or creaming—Brownian motion maintains the disperse particles in suspension (Schott. "Colloidal Dispersions", *Remington: The Science and Practice of Pharmacy*, 19$^{th}$ Ed., Mack Publishing Co.: Easton, Pennsylvania (1995)). A suspension of the invention also desirably is a coarse dispersion in which the particle size exceeds 0.5 micrometers, and preferably ranges from about 0.1 to about 150 micrometers, optionally from about 50 to about 100 micrometers. Accordingly, particle size of a suspension according to the invention optionally ranges from about 1 nanometer to about 150 micrometers, but most desirably, particle size is that expected of a colloid."

"The Tyndall effect can be used to differentiate a colloidal suspension from a true solution in cases where a beam of light can be passed through the material. In a true solution, the light passes through a material relatively unimpeded and will not be visible from the side view. In a colloidal suspension, the colloid particles are sufficiently large to significantly scatter the light and make the beam visible from the side view. True solutions are distinct from colloids in that the dispersed agents in true solutions (i.e., the solutes) are typically atoms, ions, or fairly small molecules. As mentioned previously, a chitosan-containing composition according to the invention can be either a suspension (i.e., including a colloidal suspension) or a solution (i.e., a true solution). Desirably, however a chitosan-containing composition of the invention exhibits a Tyndall effect such that the particles present in the composition scatter the light."

Accordingly, the present invention desirably provides a stable liquid suspension composition (or a chitosan-containing composition that is not a suspension) that can comprise, consist essentially of, or consist of chitosan, a non-fatty acid or salt thereof, and water or aqueous solution, wherein each are present in said composition in a stabilizing amount sufficient to effect the formation of a stable liquid suspension. Desirably the chitosan is present in this composition in an amount of from about 2.5% to about 4.0% (mass/volume) of the composition, and the non-fatty acid or salt thereof is present in an amount of from about 2.5% to about 4.0% (mass/volume) of the composition. Such a suspension prepared as described herein (and which may contain other ingredients) is described by the proprietary name "Kytabsorbe™". Preferably this composition is palatable. Optimally this composition has a pH of from about 3.6 to about 4.2, preferably a pH of about 3.8. Also, desirably this composition has a viscosity of from about 120 to about 390 centipoise, especially a viscosity of from about 200 to 300 centipoise, and particularly a viscosity of about 240 centipoise (rotational viscosity). As described in the examples which follow (particularly Example 13), preferably a composition according to the invention (i.e., a composition consisting essentially of chitosan, water or aqueous solution, and a non-fatty acid) binds at least about 3 grams of fat per gram of chitosan, desirably from about 3 to about 12 grams of fat per gram of chitosan, and optionally from about 6 to about 7 grams of fat per gram of chitosan. However, these ranges are merely exemplary of the fat binding ability of the chitosan formulations observed with use of particular fats, and particular conditions. It is likely that even higher binding capabilities (i.e., capability of binding fat, free fatty acids, cholesterol, sterols other than cholesterol, and bile acids) would be obtained with optimization of conditions, and with use of particular agents (e.g., particular fats, free fatty acids, etc.).

Preferably according to the invention, the chitosan-containing composition can contain other optional components, e.g., dietary fiber. Thus, the present invention also provides a stable liquid suspension composition that comprises (i.e., or consists essentially of, or consists of): (a) chitosan, a non-fatty acid or salt thereof, and water or aqueous solution, wherein each are present in the composition in a stabilizing amount sufficient to effect the formation of a stable liquid suspension; and (b) dietary fiber. Optionally the dietary fiber is insulin. Desirably the chitosan is present in this composition in an amount of from about 2.5% to about 4.0% (mass/volume) of the composition, the non-fatty acid or salt thereof is present in an amount of from about 2.5% to about 4.0% (mass/volume) of the composition, and the dietary fiber is present in an amount of from about 2.0% to about 10.0% (volume/volume) of the composition. Preferably this composition is palatable. Optimally this composition has a pH of from about 3.6 to about 4.2, preferably a pH of about 3.8. Also, desirably this composition has a viscosity of from about 120 to about 390 centipoise, especially a viscosity of from about 200 to 300 centipoise, and particularly a viscosity of about 240 centipoise (rotational viscosity).

Moreover, the composition can provide still further optional components, in particular, to provide a stable liquid suspension composition that preferably consists essentially of: (a) chitosan, a non-fatty acid or salt thereof, and water or aqueous solution, wherein each are present in the composition in a stabilizing amount sufficient to effect the formation of a stable liquid suspension; and (b) dietary fiber, preservative, and flavor.

Thus, the present invention optimally provides a stable liquid suspension composition that desirably consists essentially of:
(a) chitosan, a non-fatty acid or salt thereof, and water or aqueous solution, wherein each are present in the composition in a stabilizing amount sufficient to effect the formation of a stable liquid suspension; and
(b) dietary fiber, preservative, and flavor,
wherein the chitosan is present in an amount of from about 2.5% to about 4.0% (mass/volume),
the non-fatty acid or salt thereof is present in an amount of from about 2.5% to about 4.0% (mass/volume),
the dietary fiber is present in an amount of from about 2.0% to about 10.0% (volume/volume),
the preservative is present in an amount of from about 2.5% to about 4.0% (mass/volume), and
the flavor is present in an amount of from about 2.0% to about 4.0% (mass/volume) of the composition.

Preferably this composition is palatable. Optimally this composition has a pH of from about 3.6 to about 4.2, preferably a pH of about 3.8. Also, desirably this composition has a viscosity of from about 120 to about 390 centipoise, especially a viscosity of from about 200 to 300 centipoise, and particularly a viscosity of about 240 centipoise (rotational viscosity). As described in the examples which follow (particularly Example 13), preferably a composition according to the invention (i.e., a composition consisting essentially of chitosan, water or aqueous solution, a non-fatty acid or salt thereof, dietary fiber, preservative, and flavor) binds at least about 2 grams of fat per gram of chitosan, desirably from about 2 to about 10 grams of fat per gram of chitosan, and optionally from about 2 to about 5 grams of fat per gram of chitosan. However, these ranges are merely exemplary of the fat binding ability of the chitosan formulations observed with use of particular fats, and particular conditions. It is likely that even higher binding capabilities (i.e., capability of binding fat, free fatty acids, cholesterol, sterols other than cholesterol, and bile acids) would be obtained with optimization of conditions, and with use of particular agents (e.g., particular fats, free fatty acids, etc.).

When the composition of the invention has the particular formulation set out in Example 5, it is known under the proprietary name "X-Fat™".

Other characteristics of a chitosan-containing composition of the invention include that the composition is clear (i.e., meaning non-opaque). The chitosan stays in suspension.

Constituent Components of the Liquid Chitosan-Containing Compositions

In the compositions of the invention, chitosan optionally can be obtained from any possible source, e.g., from fungal walls and exoskeletons of arthropods, including but not limited to insects, crabs, shrimp, and lobsters, and by alkaline N-deacetylation of chitin. Chitosan also preferably can be purchased directly from commercial suppliers, e.g., Chitosan SC 143 and Chitosan SC 243 obtained from Natural Biopolymer Inc., Raymond, Wash. (product code 27130123, generic name "chitosan"), or other commercial vendor. Chitosan desirably can be applied in the form of chitosan, or any other appropriate form, e.g., chitin, chitosan salt (such as chitosan lactate salt). Thus, according to this invention a "chitosan" encompasses chitosan per se (i.e., that product obtained by N-deacetylation of chitin), as well as chitin, but desirably, is in the form of chitosan per se. A preferred source of chitosan according to the invention is from shrimp.

Preferably the chitosan employed in the invention is at least about 75% deacetylated, even more preferably is at least about 90% deacetylated, and optimally, is at least about 95% deacetylated. Generally, pharmaceutical grade chitosan is deacetylated between about 90 and 95%, and can absorb about 10 to 12 times its weight in fat, whereas nutritional grade chitosan is deacetylated between about 75 and 80%, and can absorb about 4 to 6 times its weight in fat. Typically, as viscosity or deacetylation of a chitosan preparation is increased, its effect on fat digestibility is increased (Deuchi et al., *Biosci. Biotechnol. Biochem.*, 59(5), 781–5 (1995)), so for greater fat absorption, an increased amount of deacetylation is preferred. Preferably the chitosan employed to make the compositions of the invention has a viscosity of from about 40 mpas to about 100 mPas, even more desirably, from about 50 to about 80 mPas. Typically the chitosan employed to make the compositions of the invention has an average molecular weight of from about 30,000 to about 300,000 daltons, and a preferred average molecular weight of from about 100,000 to about 200,000 daltons. Desirably, the mean particle size of the chitosan can be assessed, e.g., using sieve analysis. Using such an approach the particles typically pass a 40–50 industrial screen mesh and are retained by a 60–100 industrial screen mesh, having a mean size of about 80 mesh, i.e., corresponding to about 7/1000 of an inch. Of course, however, there is a distribution of particle sizes. Generally, however, it is preferred that the "grind" of chitosan is finer than that typically used, e.g., to fill capsules.

The chitosan present in the chitosan-containing compositions of the invention optimally comprises from about 2.5% to about 4.0% (mass/volume) of the liquid chitosan-containing composition of the invention, even more desirably from about 3.0% to about 3.5% (mass/volume), and especially about 3.25% (mass/volume).

The chitosan can be added to the preparation in the form of chitosan flake (e.g., ground either "course", "flake", or "fine"), chitosan powder, or solubilized chitosan. While chitosan flake and chitosan powder are commercially available, solubilized chitosan desirably can be obtained from chitosan flake and chitosan powder by solubilizing the chitosan first with an appropriate non-fatty acid or acid salt as a solubilizing agent.

According to the invention, appropriate non-fatty acids or acid salts include, but are not limited to, organic non-fatty acids or acid salts having from 1 to 10 carbon atoms, preferably from 2 to 7 carbon atoms, such as acetic acid, adipic acid, citric acid, formic acid, lactic acid, malic acid, and other appropriate non-fatty acids or acid salts, which are appropriate to disperse the chitosan without deleteriously impacting the properties of the liquid chitosan-containing composition. Generally such an acid salt or non-fatty acid is present in the chitosan-containing composition in an amount ranging from about 2.5% to about 4.0% (mass/volume) of the liquid chitosan-containing composition of the invention, even more desirably from about 3.0% to about 3.5% (mass/volume), and especially about 3.25% (mass/volume). Preferably the non-fatty acid or acid salt is present in the liquid chitosan-containing composition so as to comprise from a 1:10 mass:mass ratio with chitosan to a 10:1 mass:mass ratio with chitosan, and optimally comprises from a 1:2 to 5:1 mass:mass ratio with chitosan.

An especially preferred non-fatty acid or acid salt for use in the liquid chitosan-containing compositions of the invention is a vitamin acid, such as ascorbic acid, folic acid, pantothenic acid, biotin, etc. Particularly preferred for use in the invention are ascorbic acid, ascorbate, or a salt of ascorbic acid. Ascorbic acid (i.e., Vitamin C) can be obtained from Natural Biopolymer (Hebei, China), Roche Laboratories (La Jolla, Cailf.), or other commercial vendors. The ascorbic acid present in the formulation optimally comprises from about 2.5% to about 4.0% (mass/volume) of the liquid chitosan-containing composition of the invention, even more desirably from about 3.0% to about 3.5% (mass/volume), and especially about 3.25% (mass/volume). Desirably, ascorbic acid is present in the liquid chitosan-containing composition so as to comprise from about a 1:10 mass:mass ratio with chitosan, to about a 10:1 mass:mass ratio with chitosan, and optimally comprises about a 1:1 mass:mass ratio with chitosan. Ascorbic acid is especially preferred for use in the invention since ascorbic acid or ascorbate formulations have been shown to increase the effectiveness of chitosan (see, e.g., Kanauchi et al., Biosci. Biotechnol. Biochem., 59(5), 786–90 (1995); Bugamelli et al., Arch. Pharm. (Weinheim), 331(4), 133–8 (1998); Deuchi et al., Biosci. Biotechnol. Biochem., 59(7), 1211–6 (1995)).

Chitosan that is appropriately dispersed with a non-fatty acid and/or acid salt preferably is appropriately formulated to a desired concentration by mixing with water (e.g., aerated, oxygenated, distilled, deionized, Spring, or other) or a predominately water-based solution (i.e., an "aqueous solution", or a solution of water that optionally contains other components). Desirably the water is Spring water, particularly Spring water purchased from an appropriate commercial vendor. Any appropriate source of water can be employed, so long as the water possesses a desired level of sterility, i.e., levels that are safe for human consumption, particularly levels which are not detectable.

The amount of water or aqueous solution employed according to the invention is dependant on the concentration of chitosan and other components desired, but typically ranges from about 10 to 50 times, more preferably from about 20 to 40 times, even more desirably about 30 times the amount (weight/weight or volume/volume) of chitosan present in the liquid chitosan-containing composition. Optimally according to the invention, this admixture results in a composition or fluid in which the chitosan flakes, powder or liquid is suspended ultra-submicroscopically to create a suspension composition, as defined above. Desirably, such a suspension composition exhibits stability. Namely, desirably the chitosan remains in suspension without precipitation for at least a year, likely up to 5 years, and quite possibly, for up to 30 years, optimally at temperatures ranging from below about 30° F. to 210° F. at sea level. According to the invention, the chitosan is in suspension (i.e., as opposed to being precipitated) when it comprises a clear and light-transmissible liquid.

The liquid chitosan-containing compositions of the invention also desirably possess a source of dietary fiber. By the generic term "dietary fiber", according to the invention is meant fiber other than chitosan or a chitin-derived product, and which is appropriate for human consumption (i.e., is not deleterious to the human body) and not digested by endogenous intestinal enzymes. A preferred dietary fiber according to the invention is insulin, which is a preferred food for the lactobacilli in the intestine and can improve the balance of friendly bacteria in the bowel (Wang et al., J AppL. Bacteriol., 75 (4), 373–380 (1993), and further has cancer preventing properties (Spiller, Dietary Fiber in Health and Nutrition, Boca Raton, Flo.: CRC Press (1994); Reddy et al., Carcinogenesis, 18 (7), 1371–1374 (1997)). Addition of dietary fiber in the compositions of the invention also is desirable in that such dietary fiber tends to be filling, and in this sense, would have a positive effect on a weight control regimen.

Optimally, the dietary fiber applied in the compositions of the invention is added in soluble (i.e., liquid) form, preferably in the form of a liquid extract. In such an extract, optionally other components also are present, but preferably, the total amount of the fiber present in the extract comprises from about 40% to about 99%, desirably, from about 60% to about 75% of the total extract. Desirably, this dietary fiber (i.e., a dietary fiber extract or soluble solution) is then present in a chitosan-containing composition of the invention in an amount ranging from about 2.0% to about 10.0% (volume/volume) of the liquid chitosan-containing composition of the invention, even more desirably from about 4.0% to about 8.0% (volume/volume), and especially about 6.2%

(volume/volume). Accordingly, with use of such an extract or soluble solution, total dietary fiber present in a chitosan composition of the invention can range from about 0.8% to about 9.9% of the liquid chitosan-containing composition of the invention.

GAVEDIET™-SP produced by Colibree Company, Inc. (Aspen, Colorado) can be employed in this capacity as a source of Fructooligosaccharide (FOS), or inulin, from the Blue Agave plant. Colibree's GAVEDIET™-SP is a soluble dietary fiber/inulin obtained by the physical process of extraction and purification of the Blue Agave Plant juice. The product is a crystalline, flavor-neutral, slightly sweet syrup. Inulin/FOS has utility, e.g., as an ingredient in low fat and/or low cholesterol food, as a fat replacement (e.g., in oil, fat, and butter substitutes, and to improve mouthfeel), as a calorie reducer in food manufacturing, as a bulking and texturizing agent, etc. Inulin or FOS preferably is present in a chitosan-containing composition of the invention in an amount ranging from about 2.0% to about 10.0% (volume/volume) of the liquid chitosan-containing composition of the invention, even more desirably from about 4.0% to about 8.0% (volume/volume), and especially about 6.2% (volume/volume).

However, desirably other sources of FOS and/or inulin also can be applied in the present invention, particularly oligosaccharides having a long average chain length and enhanced fat mimetic properties. For instance, desirably chicory can be obtained from Orafti (Belgium) or Suiker Unie (Breda, The Netherlands), or Jerusalem Artichoke can be obtained from IFP (International Flavours and Fragrances, Dayton, N.J.). Also, preferably Neosugar (i.e., a synthetic FOS) can be obtained from Meiji Seika Kaisha (Japan), or Dahlia can be obtained from California Natural Products (Santa Barbara, Calif.). Optionally, also medical inulin derived from Jerusalem Artichoke, Chicory and Dahlia Dahlia can be obtained from Sigma, Aldrich (St. Louis, Mo.).

The flavor employed in the invention can be any flavor, e.g., cranberry, grape, orange, raspberry, banana, lime, lemon, cherry, grapefruit, apple, peach, tea, cola, as well as any other flavor, but desirably, is a palatable flavor that has a long shelf-life and which does not crystallize or precipitate out of the composition with prolonged storage. In some instances, it is preferable that the flavor be a meat, poultry, or fish flavor. In particular, desirably cranberry flavor (e.g., "Natural SN038222" obtained from International Flavours and Fragrances, Dayton, N.J.) can be employed in a liquid chitosan-containing composition according to the invention. The amount of flavor added can vary with the flavor employed. However, desirably the flavor comprises from about 2.0% to about 4.0% (volume/volume) of the liquid chitosan-containing composition of the invention, even more desirably from about 3.0% to about 3.5% (volume/volume), and especially about 3.25% (volume/volume).

Preferably, preservatives are added to the liquid chitosan-containing compositions according to the invention. Any suitable preservative can be employed, so long as the preservative does not negate other desirable properties of the chitosan-containing compositions. Preferred preservatives include, but are not limited to, sodium benzoate and potassium sorbate which can be obtained from any commercial supplier. Desirably these preservatives are of a high purity grade. Preferably these preservatives are obtained from Spectrum Quality Products, Inc. (Gardena, Calif., Catalog Numbers S1146 and P1408, respectively), or from Sigma-Aldrich (St. Louis, Mo., Catalog Numbers B3420 and S7420, respectively). Other appropriate preservatives are alcohol (from about 15 to about 20%), benzoic acid (about 0.1%), methylparaben (from about 0.025% to about 0.2%), propylparaben (from about 0.025% to about 0.2%), and sorbic acid (about 0.1%).

Sodium benzoate and potassium sorbate (or other appropriate preservatives) are to be employed in a liquid chitosan-containing composition of the invention of amounts ranging from about 0.01% to about 1.0% by weight (mass/volume, such as g/l) of the liquid chitosan-containing composition of the invention, even more desirably from about 0.05% to about 0.5% by weight (mass/volume), and especially about 0.1% by weight (mass/volume).

Optionally, sweeteners also can be added to the liquid chitosan-containing compositions of the invention, e.g., sweeteners such as natural sugars (e.g., glucose, sucrose, fructose) and synthetic sugars (e.g., Aspartame, etc.). A preferred flavor source according to the invention is GAVESWEET™-SP produced by Colibree Company, Inc. (Aspen, Colorado), which can be employed as a source of Pure Agave Nectar, a high fructose Agave syrup. Colibree's GAVESWEET™-SP is an all natural fructose syrup. It is obtained by the physical process of extraction and purification of naturally occurring inulin in the Blue Agave Plant, followed by an enzymatic hydrolysis process.

The product is a crystalline, flavor-neutral, very sweet syrup.

Desirably, however, other sweeteners also can be applied in the present invention, particularly other natural fructose sweeteners (especially those which do not have as high of a refined fructose content, which high fructose content has been suggested to exacerbate copper deficiency and to be associated heart disease characterized by high triglyceride levels), and especially sweeteners having a long shelf life and which do not crystallize or precipitate out of the composition with prolonged storage. Other preferred natural sweeteners that can be employed in the invention, include but are not limited to: Bee Honey (Dutch Gold Honey, Lancaster, Pa.); Organic Bee Honey (miscellaneous vendors); Barley Malt syrups (Briess Industries New York, N.Y.); deionized fruit juice (Daystar-Robinson, Lake Success, New York); Fruitrim liquid (Adept Solutions); Fruitrim powder (Adept Solutions Capitola, Calif.); Brown rice syrups (California Natural Products Santa Barbara, Calif.); Organic brown rice syrup (California Natural Products); Oat syrup (T & A Gourmet); Raw or Turbinado sugar (C & H sugar La Palma, Calif.); Sucanat (Wholesome Foods Palm Bay, Flo.); Organic Sucanat (Wholesome Foods Palm Bay, Fla.); Organic Sugar (Wholesome Foods Palm Bay, Flo.); and Evaporated cane juice (Florida Crystals Palm Beach, Flo.); Ki-Sweet (kiwi fruit sweetener, marketed on the Internet).

The chitosan-containing preparations of the invention desirably can contain other natural and man-made compounds such as would be appropriate for a particular application, e.g., other carriers, stabilizers, preservatives, active agents, flavorings, fragrances, etc., so long as these other compounds do not negate the desirable properties of the liquid chitosan-containing compositions. Especially preferred for addition according to the invention are vitamins, particularly fat-soluble vitamins, and especially vitamins A, B, D, E, and K.

Methods of Preparing the Liquid Chitosan-Containing Compositions

X-Fat™, and the other products of the invention relating to chitosan-containing compositions, optionally are produced using a proprietary process as described herein, which optimally provides a stable long-term composition such as a solution, and particularly preferably produces a stable suspension.

The liquid chitosan-containing compositions of the invention, i.e., the stable chitosan suspension compositions desirably are obtained by preparing the chitosan in such a way that a suspension is obtained. This differs from merely adding chitosan into a mixture. The order in which addition is made, and the means by which addition is carried out, is important. Desirably, the process is carried out at room temperature, although other temperatures also optionally can be employed.

In particular, preferably according to the invention, the chitosan is first "wetted" in a small amount of aqueous solution (e.g., water). Preferably, from about 0.25 to about 1.0 ml of water is employed for each gram of chitosan. The chitosan is added in a precise fashion, preferably by slowly mixing in the chitosan into a vortex that has been created by the high speed stirring of the liquid. If not added into a vortex, then desirably, the liquid is agitated in some fashion so as to prevent the chitosan merely from forming an insoluble clump at the bottom of the liquid. The forces in the liquid are most desirable for mixing the chitosan when a vortex (as opposed to another means of agitation) are employed.

Following the initial addition of the chitosan, the vortex is allowed to subside, but before it has completely ended, desirably, slow stirring of the mixture has begun. Preferably, this slow stirring is in a reverse direction as the vortex. Optimally, this stirring is done with an implement (especially a plastic implement) that has a large surface area to contact the mixture, e.g., optionally mixing is done with a plastic paddle in a commercial vat mixer. Reverse stirring is carried out in a gentle fashion until the chitosan has dispersed uniformly, optimally from about 10 minutes to 2 hours, desirably from about 10 minutes to about 45 minutes.

Desirably, acid (i.e., as described herein) is then added to the chitosan composition. The acid is added slowly and stirring of the composition preferably is gently maintained throughout this addition, and until the acid is dispersed. Optimally the gentle stirring of the mixture is continued, optimally from about 10 minutes to 2 hours, desirably from about 10 minutes to about 1 hour. Preferably this stirring is done with an implement (especially a plastic implement) having a large surface area, e.g., a paddle. The mixture is thick. With continuous gentle stirring, the thick liquid turns a golden color. Desirably, the mixture at this stage has an acidic pH (e.g., preferably between about 2 and about 4, optimally about 3.9).

The chitosan-acid composition optionally is a stable chitosan-containing suspension composition according to the invention. The chitosan-acid composition preferably may be used "as is". Alternately, the chitosan-acid composition may be used with the addition of other preferred components (e.g., dietary fiber, preservatives, and/or flavor, as described above) to comprise still other preferred stable chitosan-containing suspension compositions according to the invention.

Thus, the present invention provides a method of preparing a chitosan-containing composition of the invention, wherein the method preferably comprises:

(a) obtaining solid chitosan;

(b) wetting the chitosan with water or aqueous solution; and (c) mixing a non-fatty acid or acid salt to the chitosan and said water or aqueous solution to obtain the composition.

Where the chitosan composition comprises (e.g., consists essentially of) chitosan, water or aqueous solution, a non-fatty acid, and dietary fiber. The present invention provides a method of preparing this composition wherein the method desirably comprises:

(a) obtaining solid chitosan;

(b) wetting said chitosan with water or aqueous solution;

(c) mixing a non-fatty acid or acid salt to said chitosan and said water or aqueous solution to obtain a chitosan-acid mixture;

(d) in a separate vessel, adding water or aqueous solution;

(e) mixing dietary fiber in said separate vessel; and (f) mixing said chitosan-acid mixture with the contents of said separate vessel to obtain said composition.

In a preferred embodiment according to the invention, the chitosan-containing composition is formulated with chitosan, water or aqueous solution, non-fatty acid, dietary fiber, preservatives, and flavor in the method described herein to produce a proprietary chitosan-containing formulation (i.e., Kytabsorbe™). When the formulation has the particular ingredients set out in Example 5, this is known under the proprietary name X-Fat. However, it is anticipated that this formulation is easily modified in accordance with the teachings herein to produce other stable chitosan-containing suspension compositions. With addition of certain flavors, it is anticipated that particles may be introduced into the formulations, e.g., due to pulps from fruits, and the like. Such particles are not to be considered sediment of the chitosan-containing suspensions (and can be distinguished from sediment), but are more properly considered flavoring per se. Such flavoring particles desirably do not deleteriously impact the long-term stability of the chitosan-containing suspension composition.

Accordingly, to add other components to the chitosan-acid suspension composition, it is desirable that such components are mixed in water (or aqueous solution) in a separate vessel, and then are added to the chitosan-acid suspension. In cases where only preservatives are to be added, desirably these preservatives are mixed well in the separate vat, and then preferably added to the chitosan-containing acid suspension mixture with thorough mixing. Optimally, the amount of water or aqueous solution employed in the second vat is less than or about equal to the amount of water or queous solution that initially was employed in the chitosan-acid suspension composition.

It also is preferred that flavor and/or dietary fiber is added to the chitosan-acid suspension composition, either in the presence or absence of addition of preservative, as described above. In the case where preservative is present, desirably the preservative is first mixed in a separate vat, as previously described.

Optionally, where dietary fiber or flavor is to be added, preferably dietary fiber or flavor then is added to the second vat containing the preservative (with thorough mixing), and the contents of the second vat is added with thorough mixing to the contents of the first vat. In cases where dietary fiber or flavor is added in the absence of preservatives, then desirably dietary fiber or flavor is first mixed with water (or aqueous solution) in a separate vat (i.e., an amount of water or aqueous solution less than or equal to the amount added to the first vat), and following thorough mixing, the contents of the second vat are gently and thoroughly mixed with the contents of the first vat. In cases where both dietary fiber and flavor are added (i.e., in the presence or absence of preservative), optimally flavor is added to the mixture in the second vat last. Desirably flavor is filtered prior to its addition to reduce any particles present.

Alternately, when preservatives are not used, the dietary fiber and/or flavor desirably can simply be added to the vat containing the chitosan-acid suspension. Similarly, when preservatives are employed, desirably the preservatives (once dissolved) can be added from the second vat into the vat containing the chitosan-acid suspension, and then desirably, dietary fiber and/or flavor can be added to the same vat.

Thus, the present invention further provides a method of preparing a composition according to the invention (i.e., a composition that contains chitosan, water or aqueous solution, non-fatty acid, dietary fiber, flavor, and preservatives, wherein the method desirably comprises:

(a) obtaining solid chitosan;
(b) wetting said chitosan with water or aqueous solution;
(c) mixing a non-fatty acid or acid salt to said chitosan and said water or aqueous solution to obtain a chitosan-acid mixture;
(d) in a separate vessel, adding water or aqueous solution;
(e) mixing preservative in said separate vessel;
(f) mixing dietary fiber in said separate vessel;
(g) mixing flavor in said separate vessel; and
(h) mixing the contents of said separate vessel with said chitosan-acid mixture to obtain said composition.

Alternately, this method preferably comprises:

(a) obtaining solid chitosan;
(b) wetting said chitosan with water or aqueous solution;
(c) mixing a non-fatty acid or acid salt to said chitosan and said water or aqueous solution to obtain a chitosan-acid mixture;
(d) in a separate vessel, adding water or aqueous solution;
(e) mixing preservative in said separate vessel;
(f) mixing the contents of said separate vessel with said chitosan-acid mixture to obtain a chitosan-acid-preservative mixture;
(g) mixing dietary fiber with said chitosan-acid-preservative mixture; and
(h) mixing flavor with said chitosan-acid-preservative mixture to obtain said composition.

Optimally, the pH of the unaltered products obtained by the foregoing processes typically is acidic (e.g., between about 2 and about 4, preferably about 3.9). Optionally, the mixture obtained can at this stage is pumped through a funnel into separate packets, or is otherwise packaged.

It is preferable to this method of the invention that flavor is added to the suspension composition after the preservatives (e.g., sodium benzoate, potassium sorbate) have been added and dissolved. If the flavor is added before the preservatives and dietary fiber, it is possible that the preservatives may not thoroughly dissolve.

Characterization of the Liquid Chitosan-Containing Compositions

The liquid chitosan-containing compositions of the invention can be characterized and confirmed in terms of their constituents, for instance total fat/saturated fat or ability to bind total fat/saturated fat (e.g., by extraction), saturated fat cholesterol or ability to bind cholesterol (e.g., by gas chromatography), total carbohydrate (e.g., by calculation), dietary fiber, soluble fiber, sugars (e.g., FOS, D-fructose, D-glucose), protein (e.g., by Lowry assay), vitamin C (e.g., by titration), sodium (e.g., by outsourcing to a company that measures sodium level), chitosan (e.g., by Kjeldahl nitrogen determination), and inulin.

The chitosan-containing composition further can be assessed for total solids (e.g., $H_2O$), pH, conductivity, taste, color, dispersability in water, total aerobic plate count, yeast and mold count, *Bacillus cereus* count, total Coliform count in 1 gram, *Staphylococcus aureus* Count in 1 gram, and Salmonella Count in 25 grams, as well as for other factors.

Also lipid binding capacity of the liquid chitosan-containing compositions can be assessed using a lipid polysaccharide standard solution and adding by titration a product of the invention (e.g., "X-fat" product). The loss of lipid polysaccharide can be measured instrumentally, e.g., using a kinetic chromogenic lipid analyzer.

Other means of characterization are set out in the Examples which follow, and are known to those skilled in the art.

Use of the Chitosan-Containing Liquid Compositions of the Invention in a Weight Treatment Regimen The products of the invention all contain chitosan, which can be employed in weight reduction and/or weight control on the basis that they prevent fat from breaking down in the stomach and digestive tract, before it passes into the circulatory system. In other words, chitosan binds with fat, rendering it indigestible and preventing fat from entering the bloodstream. The fat is naturally expelled from the body. This expulsion of fat as opposed to fat absorption essentially produces a "no fat" or "reduced fat" diet when the products of the invention are used as described herein. Both a no fat diet and a reduced fat diet can (1) substantially reduce (if not entirely stop) weight gain, (2) substantially contribute to weight loss, and/or (3) substantially facilitate weight maintenance.

Thus, preferably the chitosan-containing compositions (especially the stable suspension) of the invention are employed in a weight treatment regimen. A "Weight treatment regimen" as used herein means any program employed for promoting weight loss, promoting weight maintenance, and/or preventing weight gain. Similarly, a "weight treatment composition" encompasses a chitosan-containing composition according to the invention that is employed for weight loss (i.e., helping to decrease over time an individual's weight), weight maintenance (i.e., helping to maintain over time an individual's weight), and/or prevention of weight gain (i.e., helping to prevent the sporadic consumption of a high fat/high calorie meal from resulting in a gain of weight). A weight treatment composition comprises an "effective binding amount of chitosan", i.e., an amount of chitosan as described herein, which is effective in binding fat, free fatty acids, cholesterol, sterols other than cholesterol, and/or bile acids, and which results in weight treatment when applied in a weight treatment program according to the invention. A "program" means a course of action (i.e., consumption of a weight treatment composition according to the invention) that is repeated for a period of time, e.g., desirably minimally for a period of from about one week to preferably, at most, about an individual's lifetime. The repetitiveness within a program optimally varies depending on whether the weight treatment composition is employed for promoting weight loss, promoting weight maintenance, and/or preventing weight gain.

For instance, when employed to promote weight loss, it is preferable that the weight treatment composition will be consumed on at least a daily basis (as further described below) for a period of time optimally ranging from about one week to preferably, at most, about one year. When employed to promote weight maintenance, it is preferable that the weight treatment composition will be consumed on at most a twice daily basis (as further described below) for a period of time optimally ranging from about one week to preferably, at most, about one year. When employed to prevent weight gain, it is preferable that the weight treatment composition will be consumed on an "as needed" basis (as further described below) for a period of time optimally ranging from about one week to preferably, at most, an individual's lifetime.

The chitosan-containing compositions of the invention (or variations thereof) can be applied for any ingestible beverage, e.g., water, iced tea, fruit drinks, sodas, colas, diet beverages and potions, "health" drinks, gastrointestinal cleansing systems, and the like. When employed in this fashion, the chitosan-containing compositions (e.g., present as part of another beverage) can be further changed in consistency, e.g., by freezing to create a Popsicle or slush, by mixing in a blender with chips of ice to create a smooth, cool beverage having a milkshake-like consistency, and the like. Similarly, the chitosan-containing compositions of the invention (or variations thereof) can be applied "as is", e.g., by merely drinking the compositions, or added as a component to another liquid or semi-liquid formulation not to drink, but, for instance, to be applied to the surface of another food, such as a dressing, topping, dip, garnish, or other. This preferably is employed where the other food is a non-fat food, e.g., fruit, seed, nut, and/or vegetable which is to be eaten as part of a meal with a fat and/or cholesterol-containing food. For instance, the chitosan-containing compositions can be mixed with other non-fat flavoring ingredients (e.g., vinegar, vinaigrette) and poured or sprayed over the surface of solid food for consumption. Alternately, the fruit, seed, nut, and/or vegetable, the chitosan-containing compositions, and the other liquid or semi-liquid formulation can be mixed together, e.g., to produce a soup, chili, salsa, topping, or other similar item. With careful choice of other ingredients, and with selection of a non-fatty meat, fish, or poultry, it may be possible to apply the chitosan-containing compositions as a gravy, topping, dressing, etc. for meat, fish, and/or poultry to be eaten as part of a meal with a fat and/or cholesterol-containing food.

Additionally the preferred compositions can be preformulated as, or merely added prior to consumption, to any non-fat semi-solid formulation, e.g., nonfat pudding, Jell-O, gelatin, or tofu. However, the rigidity of these formulations may be altered with addition of the products of the invention.

Chitosan is already approved for sale in tablet form and sold in various stores for weight loss/weight control. Thus, there is a large source of data already available suggesting its safety and efficacy for this use. The side effects of chitosan that have been reported appear minor (e.g., flatulence, reduction in ingestion of vitamins, etc.). Similarly, acetic acid, lactic acid, and ascorbic acid have all been safely used for human consumption. However, individuals having shellfish allergies, pregnant or lactating women, persons under eighteen years of age, and individuals on medication that is fat-soluble or whose uptake would otherwise be impaired by consumption of the chitosan-containing products of the invention should not consume X-Fat™, or any other chitosan-containing product according to the invention. For prolonged users of the present inventive chitosan products, vitamin supplements high in fat soluble vitamins (particularly vitamins A, B, D, E, and K) preferably should be taken with breakfast or at another appropriate time on a daily basis. Optimally, fat intake will be monitored to ensure the appropriate recommended grams of fat are consumed (i.e., and actually assimilated by the body) on a daily basis. Medical supervision is recommended for anyone with concerns regarding a chitosan weight loss or weight maintenance regimen. Thus, generally, use of the chitosan-containing products of the invention is preferred for those individuals who do not have a preexisting health condition that would impact use of the chitosan-containing compositions of the invention.

While X-Fat™ (and other liquid chitosan-containing compositions of the invention) has the capacity to modify fat absorption, it does not otherwise control calorie intake. Thus, while the liquid chitosan-containing compositions of the invention (including X-Fat™) when used alone should facilitate weight loss, facilitate prevention of weight gain, and/or facilitate weight maintenance, faster and/or more desirable results optimally will be obtained when the chitosan-containing compositions of the invention are used in conjunction with a calorie-controlled diet, preferably combined with exercise.

Additionally, desirably the product should be taken prior to, concurrent with, or following a meal, i.e., especially a meal containing an item selected from the group consisting of fat, free fatty acids, cholesterol, sterols other than cholesterol, and bile acids. According to the invention, a "meal" can be any food consumed by an individual, including, but not limited to, those courses of consumption known as "breakfast", "lunch", "dinner", and "snacks". By "prior to" is meant an amount of time ranging from about 10 seconds to desirably, no more than about 30 minutes prior to consumption of the meal. By "concurrent with" is meant at about, or approximately about, the same time as consumption of the meal. By following is meant an amount of time ranging from about 10 seconds to desirably, no more than about 30 minutes after the consumption of the meal. Optimally according to the invention, the product is not taken prior to, concurrent with, or following a meal that is a fat-free, or reduced fat, meal, unless the meal contains substantial amounts of cholesterol and/or bile acids. By "substantial amounts" is meant an amount of cholesterol and/or bile acid that would typically be unacceptable in a medically-approved diet for an individual having need to control consumption of cholesterol and/or bile acids.

It further is desirable according to the invention for people to discontinue use of the product for a minimum of a two week period of time following a weight loss of ten percent of starting weight, should such weight loss occur within a month. Additionally, it is preferable that a person that routinely consumes the liquid chitosan-containing compositions of the invention also ingests about 8 glasses of water each day.

The preferred dosage as described herein (see, e.g. Example 5) is of an ingestion of the liquid chitosan-containing compositions (each containing about 0.5 g of chitosan), which desirably is not to be taken more than two times in a single day.

Accordingly, the present invention provides a method of using a chitosan composition according to the invention in a subject's weight treatment program, the method desirably comprises the subject's consumption of the composition either prior to, concurrent with, or following a meal. Optimally the meal contains an item selected from the group consisting of fat, free fatty acids, cholesterol, sterols other than cholesterol, and bile acids. The present invention further provides an improved method of weight treatment, the improvement desirably comprising a subject's consumption of the composition of the invention either prior to, concurrent with, or following a meal.

Other Illustrative Uses of the Liquid chitosan-Containing Compositions

Also, as further described herein, the liquid chitosan-containing compositions of the invention can be employed in a wide variety of applications other than weight loss/ weight maintenance due to the unique properties of chitosan. This example describes but a few means by which the preparations according to the invention, or variations of these compositions, can be applied. Of course, other means are available, and would be apparent to those familiar with the properties of chitosan.

Apart from a positive effect on weight reduction, weight gain prevention, and weight control, there is evidence of other positive effects observed by persons who have used chitosan-containing products on a regular basis, e.g., control of blood pressure, improved cholesterol levels (i.e., boosted HDL cholesterol levels, reduced LDL cholesterol levels), promotion of wound healing, antibacterial effects, antiCandida effects, antiviral effects, antacid activity, inhibition of the formation of plaque/reduction in tooth decay, more rapid bone repair, improved calcium absorption, and reduced levels of uric acid (Hennen, Chitosan, Pleasant Grove, Utah.: Woodland Publishing, Inc. (1996)). The chitosan-containing compositions of the invention, while they might secondarily treat, cure, or prevent any particular disease, are primarily intended as described herein to contribute to weight loss, prevention of weight gain, and/or maintenance of a particular weight. The chitosan-containing compositions do this by helping to control fat absorption, thereby assisting weight loss, and preventing or reducing weight gain. However, the compositions of the invention also can be used as described below.

The chitosan-containing compositions can be used in a subject's cholesterol treatment program as cholesterol treatment compositions in a manner analogous to use of the composition in a weight treatment program, wherein the subject consumes the composition either prior to, concurrent with, or following a meal. As used herein, a "cholesterol treatment program" means any program employed for promoting cholesterol reduction, promoting cholesterol maintenance, and/or preventing increases in cholesterol. A cholesterol treatment composition comprises an "effective binding amount of chitosan", i.e., an amount of chitosan as described herein, which is effective in binding cholesterol, sterols other than cholesterol, and/or bile acids, and which results in cholesterol treatment when applied in a cholesterol treatment program according to the invention. A "program" is as previously defined, and desirably is carried out as described for the weight treatment program. In particular, the cholesterol treatment program can be applied where a subject consumes a meal containing an item selected from the group consisting of cholesterol, sterols other than cholesterol, and bile acids.

The chitosan-containing compositions of the invention (or variations thereof) desirably can be applied as an oral mouthwash, e.g., in the form of a fine spray mist, or the more traditional "swish-and-spit" formulation. The use of the compositions in this fashion may aid in the prevention of plaque formation and halitosis by facilitating the removal of certain compounds before they contribute to plaque and bad breath. The compositions also may aid the healing of mouth lesions, e.g., cancer sores and cold sores, by removing compounds away from and out of these sores.

The cleansing properties of chitosan further provide that chitosan-containing compositions of the invention (or variations thereof) preferably can be applied for bathing treatments for wounds and/or burns and/or any other type of lesion (preferably an external lesion), as well as additives to topical treatments for same, so long as the chitosan does not negative any other beneficial/therapeutic compounds present in the formulation.

Along the same line, optionally chitosan-containing compositions of the invention (or variations thereof) can be applied for numerous veterinary applications where its cleansing properties would prove therapeutic, e.g., as veterinary pet de-wormers or in the cleansing of any type of infestation, wound, burn, or lesion. Desirably, the flavoring employed in the composition is one that is palatable to the animal, e.g., meat or fish flavor.

Also, the chitosan-containing compositions of the invention (or variations thereof) preferably can be applied in a variety of personal cleansing regimens, e.g., formulations for removing cosmetics or cleaning skin, shampoos or hair clarifiers, or so-called "leave-in" hair, skin, or nail products to impede buildup of residues on the hair follicle, skin, or nails, that can contribute to oiliness or greasiness. When employed in this capacity, it may be desirable (but is optional) to substitute the flavoring ingredient with, for instance, a fragrance, such as are known, and commercially available.

Similarly, the chitosan-containing compositions of the invention (or variations thereof) desirably can be applied in a variety of general cleaning products, e.g., detergents, soaps, or shampoos for laundry, carpets, dish soap, dishwashers, car washes, upholstery, leather/vinyl, and the like, as well as in any general household cleaning product, e.g., glass cleaner, floor cleaner and/or wax, general detergent, kitchen and bathroom cleaners, and many others. When employed in this capacity, it may be desired that any sweetener and/or flavoring agent be omitted from the chitosan-containing compositions of the invention.

Thus, in particular it is preferred that the chitosan-containing compositions according to the invention further comprise a potion, a beverage, a mouthwash spray mist, bathing treatment for wounds and/or burns, liquid cosmetic cleaners, veterinary solutions, and others.

EXAMPLES

The following examples further illustrate the present invention but, of course, should not be construed as in any way limiting its scope.

Example 1

This Example describes preparation of a liquid chitosan-containing composition that can be used, for instance, as a lipid binder. Optimally this composition is employed as a system detoxifier (i.e., a composition that binds fat and other undesirable ingested components).

TABLE 1

| Chitosan-containing composition | |
|---|---|
| Amount | Component |
| 5.0 grams | Chitosan flake or powder or salt |
| 2.5 grams | Citric - acid and/or other acid salt or powder |
| 5.0 ounces | Fluid (e.g., water or aqueous solution) |
| 50 grains | Aspartame |
| 25 cc | mint extract |
| 25 cc | lemon extract |
| 25 cc | orange extract |
| 50 cc | color & preservative |

In Table 1, the amounts and types of flavor extract (e.g., mint, lemon, orange) and sweetener can be varied, or omitted, depending on the desired taste and smell of the resulting composition. Similarly the amount and inclusion of color and preservative is optional.

The composition is obtained by placing the chitosan flake, powder, or salt admixed with the acid(s) powder or salt in a measuring cup, adding 5 ounces of fluid, stirring briefly for 10 to 20 seconds, leaving the mixture sitting until for up to about 10 minutes or until all the chitosan has dissolved. In this method, the chitosan and citric acid salt dissolve into ultramicroscopic particles suspended in the composition. At this stage, other components that impact taste, appearance, smell, or other properties of the chitosan-containing mixture can be added. For instance, as set out in Table 1, a sweetener such as Aspartame can be added to or pre-mixed with the chitosan-containing composition, along with various flavoring extracts. Then, the mixture is either shaken or stirred until the mixture is evenly suspended. Refrigeration of the chitosan-containing composition is optional, and it can be stored for future use.

The chitosan-containing composition can be used by pouring one ounce of the mixture of Table 1 into liter- or quart-sized containers along with other liquids or compositions intended for human (or mammal) consumption, and mixing well. Preferably the liquids or compositions do not contain a fatty bile acid or compound. Thus, the composition of Table 1 provides five applications of 1 ounce each that are ready for use.

Example 2

This Example describes preparation of a liquid chitosan-containing composition that can be used, for instance, as a lipid binder and/or system detoxifier. Optimally the composition exhibits favorable effects on virility, or a person's perception of virility following consumption of the composition.

TABLE 2

Chitosan-containing composition

| Amount | Component |
| --- | --- |
| 5.0 grams | Chitosan flakes or powder |
| 2.5 grams | Lactic acid and/or other ingestible salt/powder |
| 5.0 ounces | Fluid (e.g., water or aqueous solution) |
| 2.0 grams | Rhodiola Rosea salt |
| 25 cc | Vanilla extract |
| 25 cc | Mint extract |
| 25 cc | Lemon extract |
| 25 cc | Orange extract |
| Optional | Color & preservative |

In Table 2, the amounts and types of flavor extract (e.g., mint, lemon, orange) can be varied, or omitted, depending on the desired taste and smell of the resulting composition. Similarly the amount and inclusion of color and preservative is optional.

The composition is obtained by placing the chitosan flake or powder admixed with the acid(s) powder or salt in a measuring cup, adding 5 ounces of fluid, stirring briefly for 10 to 20 seconds, leaving the mixture sitting until for up to about 10 minutes or until all the chitosan has dissolved. In this method, the chitosan and acid salt dissolve into ultra-microscopic particles suspended in the composition. At this stage, other components that impact taste, appearance, smell, or other properties of the chitosan-containing mixture can be added. For instance, as set out in Table 2, Rhodiola Rosea salt can be added to or pre-mixed with the chitosan-containing composition, along with various flavoring extracts. Then, the mixture is either shaken or stirred until the mixture is evenly suspended. Refrigeration of the chitosan-containing composition is preferable (but not necessary), and it can be stored for future use.

The chitosan-containing composition can be used by pouring one ounce of the mixture of Table 2 into liter- or quart-sized containers along with other liquids or compositions intended for human (or mammal) consumption, and mixing well. Preferably the liquids or compositions do not contain a fatty bile acid or compound. Thus, the composition of Table 2 provides five applications of 1 ounce each that are ready for use.

The beverage mixtures in this and the foregoing Example optionally can be modified to include further agents, including but not limited to, other natural or man-made, non-fatty compounds, element or acids, such as dehydroepiandrosterone (DHEA), or, oligomeric proanthocyanidin (OPC), etc.

Example 3

This Example describes preparation of a liquid chitosan-containing composition that can be used, for instance, in burn/wound topical applications.

TABLE 3

Chitosan-containing composition

| Amount | Component |
| --- | --- |
| 30 grams | Chitosan |
| 15 grams | Lactic acid salt (or other acid salt such as acetic acid salt) |
| 5 ounces | Distilled or filtered water |
| 50 cc | Soluble mild gel extract |
| Optional | Color & preservative |

In Table 3, the amounts and types of color and preservative can be varied, or omitted.

The composition is obtained by placing the chitosan flake admixed with the acid(s) salt in a measuring cup, adding 5 ounces of fluid, stirring briefly for 30 seconds, leaving the mixture sitting until all the chitosan has dissolved. In this method, the chitosan and acid salt dissolve into ultramicroscopic particles suspended in the composition.

At this stage, other components that impact appearance or other properties of the chitosan-containing mixture can be added. For instance, as set out in Table 3, a mild soluble gel can be added to or pre-mixed with the chitosan-containing composition (i.e., to facilitate application). Optionally, other therapeutic agents also can be present in the gel. Then, the mixture is stirred until evenly mixed. The chitosan-containing composition can be stored for future use.

Example 4

This Example describes preparation of a liquid chitosan-containing composition that can be used, for instance, in weight reduction, as well as in other applications, for instance, in veterinary applications such as animal deworming.

TABLE 4

Chitosan-containing composition

| Amount | Component |
| --- | --- |
| 20 grams | Chitosan |
| 12 grams | Formic acid salt/citric acid powder/salt |
| 5 ounces | Distilled or filtered water |
| 50 cc | Meat extract or flavoring (not containing fat) |
| 50 cc | Chicken extract or flavoring (not containing fat) |
| 50 cc | Color |
| Optional | Preservative |

In Table 4, the amounts and types of color and preservative can be varied, or omitted. Similarly, the amount and types of extracts and flavoring agents can be varied.

The composition is obtained by placing the chitosan admixed with the acid(s) powder/salt in a measuring cup, adding 5 ounces of fluid, stirring briefly for 30 seconds, leaving the mixture sitting until all the chitosan has dissolved. In this method, the chitosan and acid salt dissolve into ultramicroscopic particles suspended in the composition.

At this stage, other components that impact taste, smell, or other properties of the chitosan-containing mixture can be added. For instance, as set out in Table 4, extracts or flavoring agents can be added to or pre-mixed with the chitosan-containing composition (i.e., to increase palatability). Then, the mixture is stirred until evenly mixed. The chitosan-containing composition can be stored for future use.

Example 5
Preparation of a Liquid Chitosan-Containing Composition

About 30 ounces of chitosan-containing suspension composition ("X-fat") can be prepared, and, for instance, packaged into 60×0.5 ounce packets or other conveniently-sized packets using the following formulation:

TABLE 5

Chitosan composition formulation (approximately 30 liquid ounces)

| Component | Amount | Conversion |
|---|---|---|
| Chitosan | 1.050 mass ounces | (=30 grams) |
| Ascorbic Acid | 1.050 mass ounces | (=30 grams) |
| Spring Water | 27.000 liquid ounces | |
| Cranberry Flavor | 1.000 liquid ounces | |
| Inulin | 2.000 liquid ounces | |
| Sodium Benzoate | 0.035 mass ounce | |
| Potassium Sorbate | 0.035 mass ounce | |

This can be scaled up, for instance to a commercial vat size of about 80 liters, as follows:

TABLE 6

Chitosan composition formulation (approximately 80 liters)

| Component | Amount | Conversion |
|---|---|---|
| Chitosan | 2.382 kilograms | |
| Ascorbic Acid | 2.382 kilograms | |
| Spring Water | 63.879 kilograms | (=16.84 gallons) |
| Cranberry Flavor | 2.366 liters | |
| Inulin | 4.732 liters | |
| Sodium Benzoate | 79.39 grams | |
| Potassium Sorbate | 79.39 grams | |

All mixing of the components to obtain a chitosan-containing composition is done at room temperature. The formulation is obtained by slowly mixing in the chitosan into a vortex created by the high speed stirring of spring water (e.g., 16 oz. for a 30 oz. formulation) present in a vat ("Vat A"). The mixture is reverse stirred gently with a plastic paddle until the chitosan has dispersed uniformnly. This generally takes less than an hour. Ascorbic acid is then added slowly and stir-red gently until dispersed. This forms a viscous material that is best stirred with a paddle. The thick liquid turns a golden color with continuous gentle stirring (i.e., generally less than an hour). Typically the mixture at this stage has an acidic pH (e.g., between about 2 and about 4, typically about 3.9).

Into a separate vat ("Vat B") is added spring water (e.g., 11 oz. for a 30 oz. formulation). The preservatives are added to Vat B and mixed well. Then the contents of Vat B are added to Vat A, and the liquid is mixed with slow stirring. Next the inulin is added, and the reaction is gently and thoroughly mixed. The cranberry flavor is added through a filter (or first filtered and then added), and mixed thoroughly. The pH of the unaltered product obtained by this process typically is acidic (e.g., between about 2 and about 4, typically about 3.9). Optionally, the mixture can at this stage is pumped through a funnel into separate packets.

It is important to this process that the cranberry flavor is added after the preservatives (sodium benzoate, potassium sorbate) have gone into solution. If the cranberry flavor is added before the preservatives and inulin, the later added preservatives will not go into solution. This process similarly can be carried out with use of acids other than ascorbic acid, and with other dietary fiber, or omitting dietary fiber. Similarly the flavor can be varied.

Example 6
Assessment of Components of Chitosan-containing Samples

These studies were carried out to assess various characteristics of chitosan suspension samples prepared according to Example 5.

For these experiments, all analyses were conducted by Gibraltar Laboratories, Inc., Fairfield, N.J., a biological research and regulatory testing service that conducts testing of biological samples using established research practices. Results of such testing for three separate chitosan drink samples synthesized according to the invention are set out in Table 7 below.

TABLE 7

Summary of Chemical Analysis of Three Chitosan-Containing Samples

| Analysis | Sample 1 | Sample 2 | Sample 3 |
|---|---|---|---|
| Water | 88.6% | 88.78% | 88.78% |
| Ash | 0.11% | 0.33% | 0.17% |
| Fat | 0% | 0% | 0% |
| Protein | 0 mg/gm | 0 mg/gm | 0 mg/gm |
| Chitosan | 2.84% | 2.38% | 2.58% |
| Carbohydrate | 11.29% | 10.89% | 10.87% |
| Ascorbic Acid | 3.34% | 3.23% | 3.31% |
| Cholesterol | <1.0 mg/100 g | <1.0 mg/100 g | <1.0 mg/100 g |
| Total Dietary Fiber | 8.51 | 7.91 | not tested |
| Total Soluble Dietary Fiber | 3.57 | 3.30 | 2.99 |
| Iodine | 0 | 0 | 0 |
| Calories | 45.2 C/g | 43.6 C/g | 43.5 C/g |

The protein could not determined by standard Kjeldahl nitrogen analyses due to chitosan interference. The Bradford protein determination method was used instead. Interference similarly was obtained with use of the Lowry assay attempted by two methods. Similar results as presented in Table 7 were obtained from other sample analyses.

Example 7
Assessment of Microbial Concentration in Chitosan Compositions

These studies were carried out to determine the aerobic plate count of two separate chitosan liquid samples prepared in accordance with Example 5 as well as the presence/absence of specific USP Indicator Organisms.

For these studies, the USP Microbial Limits Test was carried out by adding 10 mL of sample to 90 mL of GBL STAT Broth (Trypticase Soy Broth containing 4% Tween 20, 0.5% lecithin, and 1% lactose). The jar was shaken to give a 1:10 suspension (enrichment). Suitable aliquots were plated with GBL STAT Agar (Trypticase Soy Agar containing 4% Tween 20 and 0.5% lecithin) for bacterial counts (30 to 35° C./48 to 72 hours). The above 10 mL enrichment was then incubated at 30 to 35° C. for 48 to 72 hours and subcultured to selective and differential media (30 to 35° C./24 to 48 hours) as cited in USP.

The results of these tests confirm that the chitosan suspension samples each harbored a bacterial count of less than about 10 cfu/ml, and a mold/yeast count of less than about 10 cfu/ml. *Escherichia coli* and *Salmonella sp.* were not detected in the 10 mL enrichment. When tested for, *Pseudomonas aeruginosa* and *Staphylococcus aereus* similarly were not detected. Similar results were obtained from other sample analyses.

Similar results were obtained in experiments performed according to a USP 23 methodology. The media for this method are as follows: U.S. Patent Modified Lactose Broth (MLB) A32; U.S. Patent Modified Trypticase Soy Broth (MTSB) A1; GBL STAT Broth A2, TSB A5; Selenite Cysteine Broth (SCB) A57*; Tetrathionate Broth (TB) A74; GBL STAT Agar A32; Sabouraud Dextrose Agar (SDA)L67; Mannitol Salt Agar (MSA) K140; MacConkey's Agar (MAC) A9; Cetrimide Agar (CET) K68; Xylose Lysine Sesoxyeholate Agar (XLD) A29; and BGA A64.

The abbreviations of the media are: MLB (i.e., Lactose Broth containing 4% Tween 20 and 0.5% Lecithin); MTSB (i.e., Trypticase Soy Broth (TSB) containing 4% Tween 20 and 0.5% Lecithin); GBL Stat Broth (i.e., TSB containing 4% Tween 20 and 0.5% lecithin); TSB (i.e., Soybean Casein Digest Broth); SDA (i.e., Sabouraud Dextrose Agar); and STAT Agar (i.e., TSA containing 4% Tween 20+0.5% Lecithin).

The USP 23 methodology was carried out as follows:
1. A 1:10 dilution of the test material in MTSB (25 mL of test material +225 mL of MTSB) was prepared. The test material-broth dilution was subdivided aseptically into four- 15 mL portions in sterile test tubes.
2. A 1:10 dilution of the test material in MLB (25 mL of test material +225 mL of MLB) was also prepared. The test material-broth dilution was subdivided aseptically into two-15 mL portions in sterile test tubes.
3. The indicator organism cultures grown at 30 to 35° C. for 24+/−8 hours in TSB were diluted 1:10,000 ($10^4$) in sterile physiological saline (*Candida albicans* and *Aspergillus niger*, were diluted 1:100, $10^2$). One mL of each organism was inoculated separately into the 15 mL portions of the test material from steps I and 2 and mixed. The MTSB tubes (step 1) were inoculated separately with *Pseudomonas aeruginosa, Staphylococcus aureus, Candida albicans*, and *A. niger*. The MLB tubes (step 2) were inoculated separately with *Salmonella choleroaesuis* and *Escherichia coli*.
4. To validate that the test broth media could promote the growth of the indicator organisms grown in step 3 above, one mL of each organism diluted as in step 3 was inoculated separately into the 15 mL of MTSB and MLB (controls). The MTSB control tubes were inoculated separately with *Pseudomonas aeruginosa, Staphylococcus aureus, Candida albicans*, and *A. niger*. The MLB control tubes were inoculated separately with *Salmonella choleroaesuis* and *Escherichia coli*.
5. The number of organisms inoculated into the test material and into the controls was determined by ten-fold serial dilutions ($10^{-1}$ to $10^{-3}$) into GBL Stat Broth (TSB containing 4% Tween 20 and 0.5% lecithin). Pour plates were made from each dilution with TSA (bacteria) and SDA (fungi). The plates were incubated for 48 to 72 hours at 30 to 35° C. (bacteria) or 20 to 25° C. for 5 to 7 days (fungi) and colony forming units were counted on a darkfield Quebec colony counter.
6. 15 mL portions of the inoculated MTSB test material from step 3 (except *Candida albicans* and *A. niger*) and 15 mL portions of the inoculated MTSB broth controls from step 4 were then incubated for 48 to 72 hours at 30 to 35° C. (bacteria) or 20 to 25° C. for 5 to 7 days (fungal).
7. 15 mL portions of the inoculated MLB test material from step 3 and the 15 mL portions of the inoculated MLB broth controls from step 4 were then incubated for 24+/−8 hours at 30 to 35° C. After 24+/−8 hours at 30 to 35° C. incubation one mL of the enrichment (MTSB and MLB, *Salmonella choleroaesuis* only) was transferred into 10 mL SCB and one mL of the enrichment was transferred into 10 mL TB. The MLB, SCB and TB were then incubated at 30 to 35° C. for 12 to 24 hours.
8. The enrichments from steps 6 and 7 were then observed for gross-turbidity and a loopful of the broth was then streaked onto selective media to confirm the growth of the indicated organisms.

When studied by a USP 23 methodology, inhibition was noted. Inhibition was observed when small numbers of the above-referenced organisms were deliberately inoculated into the chitosan preparation. The interpretation of this result was that either the preparation itself or the constituents of the USP 23 microbial limits test were toxic to the presence of the low numbers of the microorganisms. It is known that the USP subculture components Fluid Tetrathionate Broth and Selenite Cystine Broth are toxic to low numbers of organisms and, as a result of this, the inhibition noted was not surprising. Should any microorganisms possibly be present in the any composition prepared according to the invention, the level is so low as to be insubstantial. The results obtained with the USP Microbial Limits Test demonstrates the absence of the above microorganisms.

In conclusion, the data confirm the absence of pathogens and the low numbers, if any, if microorganisms present in the chitosan compositions prepared according to the invention. These results confirm that the chitosan-containing compositions of the invention are substantially sterile.

Example 8

Assessment of Effect of Storage on the Liquid Chitosan-Containing Compositions

This example sets forth the effect of storage on the chitosan-containing samples prepared according to Example 5, i.e., whether the samples can be maintained for an extended period of time without showing microbial growth.

For these studies, samples were employed that been (1) maintained non-refrigerated for at least a year ("Sample A"), (2) maintained refrigerated for at least a year ("Sample B"), or (3) recently manufactured ("Sample C"). 25 mL of sample were added to 225 mL of GBL STAT Broth (Trypticase Soy Broth containing 4% Tween 20, 0.5% lecithin, and 1% lactose). The jar was shaken to give a 1:10 dilution (enrichment). Suitable aliquots were plated with GBL STAT Agar (Trypticase Soy Agar containing 4% Tween 20 and 0.5% lecithin) for bacterial counts (30 to 35° C. for 48 to 72 hours) and with Sabouraud Dextrose Agar (SDA) for mold/yeast counts (20 to 25° C. for 7 days). The above enrichment was then incubated at 30 to 35° C. for 48 to 72 hours and subcultured to selective and differential media (30 to 35° C./24 to 48 hours) as cited in USP.

25 mL of the samples were filtered through a sterile 0.2 micron membrane filter and washed three times with 100 mL of 0.1% Peptone Water. The filter was plated onto m-Endo Agar. The plates were incubated at 30 to 35° C. for 24 to 32 hours and observed for typical coliform morphology (i.e., colonies with a metallic sheen).

TABLE 8

Results of USP Microbial Limit Preparation Test

| Analysis | Sample A (maintained non-refrigerated for about a year) | Sample B (maintained refrigerated for about a year) | Sample C (freshly synthesized sample) |
|---|---|---|---|
| Bacteria (cfu/mL) | <10 | <10 | not tested |
| Mold (cfu/mL) | <10 | <10 | $1.7 \times 10^6$ |
| Coliforms (cfu/25 mL) | <1 | <1 | <1 |
| Escherichia coli | 0 | 0 | 0 |
| Salmonella sp. | 0 | 0 | 0 |
| Pseudomonas aeruginosa | 0 | 0 | 0 |
| Staphylococcus aereus | 0 | 0 | 0 |

These results confirm that the products of the invention are stable with long term storage, even in the absence of refrigeration.

Example 9

Assessment of the Viscosity and pH of the Liquid chitosan-Containing Compositions 10 This example sets forth an assessment of the viscosity and pH of the liquid chitosan-containing samples of the invention.

Representative chitosan samples prepared in accordance with Example 5 were assessed for viscosity (i.e., rotational viscosity using a Brookfield viscometer) and pH (i.e., pH meter). Mean viscosity was determined to be 241.50 centipoise (3 samples) with an upper and lower standard limit, respectively, of 390 and 120 centipoise. Average pH was determined to be 3.8.

Example 10

Assessment of the In Vitro Fat Binding Ability of the Liquid chitosan-Containing Compositions This example sets forth an assessment of the fat-binding ability of the liquid chitosan-containing samples of the invention prepared as in Example 5.

For these studies, 15 mL of melted ice cream was placed into beakers. In some of the beakers, 30 mL of water was added. In the others, 7.5 mL of a chitosan sample and 22.5 ml of water were added. The resulting mixtures were centrifuged. The material treated with the chitosan-containing composition gave a clear solution on centrifugation with the fat staying at the top of the solution. The untreated material gave a cloudy solution. 20 mL aliquots from the supernatants (i.e., the clarified solution obtained for the chitosan treated sample, and the cloudy solution obtained for the untreated sample) were then extracted using the conditions as outlined in the Associate Official Analytical Chemists Manual for the determination of fat in ice cream. The resulting extracts were evaporated and the amount of fat recovered was determined.

TABLE 9

Results of Fat Reduction Assay

| Beaker # | Type (Chitosan sample added or not) | Weight of Beaker + Extract (gm) | Weight of Beaker (gm) | Weight of Extract (gm) | % Fat Lost |
|---|---|---|---|---|---|
| 1 | – | 81.9472 | 81.5555 | 0.3917 | NA |
| 2 | – | 89.7923 | 89.5883 | 0.2040 | NA |
| 3 | – | 81.4627 | 81.2204 | 0.2423 | NA |
| 4 | + | 78.6295 | 78.5669 | 0.0626 | 77.6 |
| 5 | + | 78.8182 | 78.9460 | 0.1278 | 54.2 |
| 6 | + | 82.9954 | 83.0758 | 0.0804 | 71.2 |

NA = Not Applicable.

Calculation $$\% \text{ Loss} = \frac{(\text{average weight of Fat in untreated extracts} - \text{Weight of Fat in each treated extract}) \times 100}{\text{Average weight of fat in untreated extracts}}$$

These results confirm that the method can be used to show the level of fat absorption by the chitosan-containing composition of the invention.

Example 11

Use of the Liquid chitosan-Containing Compositions in a Weight Reduction and/or Weight Maintenance Regimen This example sets forth the manner in which the liquid chitosan-containing compositions can be employed on a routine basis to either prevent increases in weight gain, bring about weight reduction, and/or help maintain a preferred weight.

Use of the liquid chitosan-containing compositions (e.g., as described in Example 5) generally is as follows. Before one of an individual's two largest meals of the day (e.g., typically lunch or dinner), about 0.5 ounces of the liquid product (i.e., approximately 14 drops) is mixed into at least about 2 ounces of water. It is preferred that the composition be mixed in water, as the chitosan-containing product will nearly immediately begin binding with any fat (or perhaps other large, complex molecules) present in the liquid, which could have a negative impact on the appearance of the drink. However, the composition can be mixed with another drink, so long as drinks with milk, cream or fats are avoided, and preferably so long as the drink is fat free.

Following mixing, the drink is consumed. The consumption of the chitosan as a liquid (i.e., as opposed to a tablet), followed by the consumption of still further liquid has the added advantage of tending to fill the stomach, which might also help reduce intake.

Typically a "chalky" aftertaste is experienced. This likely indicates the liquid chitosan-containing product has begun collecting fat (e.g., residues on tongue and inside the mouth). It is recommended, e.g., to facilitate digestion as well as sensation, that the consumption of the product is followed by the consumption of another glass of water.

Following ingestion of the chitosan-containing product, an individual can partake of a meal in a typical fashion. The use of the chitosan-containing product can then be repeated prior to the other largest meal of the day.

Example 12

Use of the Liquid chitosan-Containing Compositions—Double Blind Clinical Study

This Example describes clinical studies for confirming the effect of a chitosan-containing composition of the invention (e.g., prepared as described in Example 5) on fat absorption.

This study is double-blind, randomized, and includes a crossover to evaluate the effect of the chitosan-containing compositions on post-prandial changes in lipids and lipoproteins, and serum triglyceride levels following a standardized fatty meal (consisting of a half cup of Haagen Daz vanilla or chocolate ice cream) in normal subjects.

Preferably the study involves twenty patients, male or female, between 21 and 60 years of age. Subjects are selected who do not have a documented history of hypertriglyceridemia, and who have not been on a low fat diet (≦30% fat, ≦300 mg cholesterol) for at least the past four weeks. It further is necessary for inclusion in the clinical study that the subject: has normal fasting plasma triglycerides ≦250 mg/dl and fasting plasma total cholesterol >220 mg/dl; has not taken lipid-lowering drugs within the four weeks prior to the determination of the qualifying lipid levels; has not taken any of the prohibited treatments hormone therapy (estrogen doses >0.03 mg), immunosuppressive agents, and chronic administration of corticosteroids (except topical or inhaled) within 2 weeks prior to the study; does not have active liver disease (i.e., elevations in AST or ALT are less than or equal to 1.5 the normal range); has a serum creatinine less than or equal to 1.2 mg/dl; has a CPK that is less than or equal to two times the normal range.

Any of the following are criteria that exclude a subject from participation in the clinical study: an acute myocardial infarction or cerebrovascular accident within 3 months; a coronary artery bypass surgery or PTCA within the past 3 months; an unstable cardiovascular condition (unstable angina, congestive heart failure, NYHA grade III or IV); a history of clinically significant gastrointestinal disease within the past 3 months; a history of liver disease or a history of biliary tract disease without a cholecystectomy; known Type I or Type II diabetes or fasting glucose >140 mg/dl; a malignancy except for cutaneous squamous or basal cell cancers; a body mass index >37 kg/m$^2$; subject is taking oral anticoagulant therapy or has abnormal prothrombin time; active psychoses; an untreated hypothyroid condition (>the upper normal limit for TSH); a history of chronic or acute drug or alcohol abuse during the past 6 months; an allergy to shell fish or iodine; abnormal cholesterol (>220 mg/dl) or triglyceride (>250 mg/d) levels; taking fat soluble medication; a possibility of pregnancy in the next 6 months.

The post-prandial test proceeds in the following steps. Blood is drawn for the first lipid test (0 hours post meal) and for laboratory safety tests. The subject consumes the standard fatty meal within 30 minutes of this 0 hour blood draw. Immediately after the meal, the subject consumes the chitosan-containing composition of the invention mixed in 2 oz of water, followed by an additional 6 oz of water. Blood is drawn for lipid testing 4 to 4 ½ hours after the meal. The blood samples are analyzed for a variety of tests, e.g., chemistry (such as sodium, potassium, calcium, glucose, BUN, creatinine, total protein, alkaline phosphate, gamma GT, SGOT (AST), SGPT (ALT), albumin, total bilirubin, uric acid, and CPK), urine chemistry (such as urine appearance, urine pH, specific gravity, urinary protein, urinary glucose, urinary ketones, urinary bilirubin, urinary red blood cells, urinary white blood cells, and casts), hematology (such as white blood cells, red blood cells, hemoglobin, hematocrit, platelet count, monocytes, eosinophils, basophils, neutrophils, and lymphocytes), and other tests (such as insulin, TSH screen, serum β-hCG).

Double-blind, randomized, patients are treated one week with the chitosan-containing composition and the other week with the placebo.

Based on confirmed properties of chitosan, these studies should validate the effectiveness of the chitosan compositions of the invention on impeding fat absorption.

Example 13

Assessment of Fat Binding and Particle Analysis

This Example sets forth an assessment of the fat binding and particle analysis for a chitosan suspensions prepared according to the invention.

A chitosan/acid/water suspension was prepared essentially as described in Example 5 for preparation of "Vat A", with the addition of further water to make up the volume. Namely the chitosan/acid/water contained about 3% mass/volume of chitosan, and about 3% mass/volume of acid, and (apart from water) no additional components. The acid employed for making the chitosan/acid/water suspension was either ascorbic acid or citric acid.

An acid-containing "complete" suspension was prepared essentially as described in Example 5 for preparation of the complete formulation (i.e., including other agents in addition to chitosan and acid). The acid employed for making the acid-containing "complete" suspension was either ascorbic acid or citric acid.

An acid-containing "complete" suspension minus chitosan was prepared essentially as described in Example 5 for preparation of the complete formulation (i.e., including other agents in addition to chitosan and acid), except that chitosan was omitted from the formulation and the difference (if any) in volume was adjusted with water. The acid employed for making the acid-containing "complete" suspension minus chitosan was either ascorbic acid or citric acid.

An aged sample was prepared essentially as described for the preparation of the chitosan/acid/water suspension using citric acid. The sample had been maintained at about room temperature for about 5 months, and then stored at about 4° C. for about 5 months.

Additionally, a control containing inulin only in the same percentage as that described in Example 5 was studied.

Fat Binding was assessed as follows. 15 ml of the sample tested was added to 5 g extra virgin olive oil and 10 ml 0.01 N hydrochloric acid. It was shaken on a Burrell wrist action shaker for 2 hours at approximately 22° C. The mixture were brought to pH 7.4 with NaOH, and was reshaken for 30 minutes as described above. Then, the tubes were centrifuged at 10,000 r.p.m. for 20 minutes in a Sorvall RC2B centrifuge at 20° C. degrees. The supernatant oil was aspirated and weighed.

Particle Analysis was performed as follows. The study was done on a Hyac Royco Model 3000A Particle Size Analyzer. The samples were diluted in sterile water for irrigation 1:100 and 1:1000. 5 ml samples were tested in the instrument and the amount of particles greater than 25, and greater than 10 microns, were measured by laser light obscuration.

Results of these studies are reported in Table 10.

TABLE 10

Fat Binding and Particle Analysis

| Sample | Particle Analysis (1:100 Dilution) | | | Particle Analysis (1:1000 Dilution) | | | Binding Capacity (Factor = g Fat Bound/g Chitosan) |
|---|---|---|---|---|---|---|---|
| | >10 $\mu$m | >25 $\mu$m | Total particles >10 $\mu$m/mL | >10 | >25 | Total particles >10 $\mu$m/mL | |
| Water | 5 | 4 | not tested | not tested | not tested | not tested | not tested |
| Chitosan/Ascorbic Acid/Water Suspension | 183 | 11 | $1.83 \times 10^4$ | 41 | 2 | $4.10 \times 10^4$ | 6.8 |
| Chitosan/Citric Acid/Water Suspension | 784 | 49 | $7.84 \times 10^4$ | 99 | 8 | $9.90 \times 10^4$ | 6.9 |
| Ascorbic Acid-Containing "Complete" Suspension | 12559 | 696 | $1.26 \times 10^6$ | 1202 | 79 | $1.20 \times 10^6$ | 2.7, 4.9 |
| Citric Acid-Containing "Complete" Suspension | 7200 | 230 | $7.20 \times 10^5$ | 557 | 12 | $5.57 \times 10^5$ | 4.3, 3.3 |
| Ascorbic Acid-Containing "Complete" Suspension Minus Chitosan | 144 | 16 | $1.14 \times 10^4$ | 56 | 5 | $5.60 \times 10^4$ | not tested |
| Citric Acid-Containing "Complete" Suspension Minus Chitosan | 138 | 11 | $1.38 \times 10^4$ | 86 | 4 | $8.60 \times 10^4$ | not tested |
| Aged Sample | 108 | 8 | $1.08 \times 10^4$ | 42 | 2 | $4.20 \times 10^4$ | 2.4 |
| Inulin Sample | 53 | 3 | $5.3 \times 10^3$ | 299 | 1 | $2.90 \times 10^4$ | not tested |

As can be seen from this Table, the chitosan/acid/water suspensions all contained particles having a size greater than 10 microns. By comparison, a "water" control did not. The amount of particles obtained with a chitosan/acid/water suspension made with ascorbic acid appeared roughly equivalent to those obtained with a suspension made with citric acid. The ascorbic acid-containing and citric acid-containing chitosan/acid/water suspension exhibited a similar ability to bind fat—about 6.8–6.9 grams of fat bound per gram of chitosan present in the suspension.

The acid-containing "complete" suspension made with either ascorbic acid or citric acid exhibits a higher particle count and similar range of binding capacity as the comparable chitosan/acid/water suspensions. However, when the "complete" formula is made without the chitosan, the particle count drops to the level that chitosan gave in the comparable chitosan/acid/water suspensions. This means that chitosan particle formation (particle suspension) is even higher when used in the "complete" formula under the conditions of the present experiment, and suggests that the particles measured are those of additional ingredients not assayed in the experiment.

While the protocol was done the same for all samples, it was not optimized to show maximum binding efficiency. It has been demonstrated that the type of dietary fat influences the effect exerted by chitosan on lipid absorption, as described, for instance, in Ikeda et al., *J. Nutr.*, 119(110), 1383–7 (1989). Accordingly, the results in Table 10 are merely exemplary of the fat binding ability of the chitosan formulations of the invention, and do not illustrate the full potential of the formulations. It is entirely possible that even higher binding capacities would be obtained with use of particular fats, free fatty acids, cholesterol, sterols other than cholesterol, bile acids, and the like.

The "aged" formula gave comparable particle results as the chitosan/acid/water suspensions. This demonstrates that the present method of obtaining a chitosan suspension is reproducible.

Example 14

Assessment of Suspended Particles of Stored Sample

This Example describes the colloidal features of a stored chitosan suspension sample.

The chitosan suspension sample was the "aged" sample described in Example 13. Visual examination of the liquid showed a profound Tyndall effect. The liquid showed Brownian motion of particles without any settling of the particles. This confirms the stability of the suspension over time.

All of the references cited herein are hereby incorporated in their entireties by reference.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. A stable liquid composition consisting essentially of chitosan, a non-fatty acid or salt thereof, and water or aqueous solution, wherein each are present in said composition in a stabilizing amount sufficient to effect the formation of a stable liquid composition.

2. The composition of claim 1, wherein said composition is stable for at least about 12 months of being maintained at a temperature from about 0° C. to about 100° C.

3. The composition of claim 1, wherein said composition contains particles of sizes of from about 1 nm to about 150 microns.

4. The composition of claim 1, wherein said composition has a viscosity of from about 120 centipoise to about 390 centipoise.

5. The composition of claim 1, wherein said composition has a pH of from about 3.6 to about 4.2.

6. The composition of claim 1, which binds at least about 3 grams of fat per gram of chitosan.

7. The composition of claim 1, wherein said chitosan is present in an amount of from about 2.5% to about 4.0% (mass/volume) of said composition.

8. The composition of claim 1, wherein said non-fatty acid or salt thereof is present in an amount of from about 2.5% to about 4.0% (mass/volume) of said composition.

9. The composition of claim 1, wherein said non-fatty acid or salt thereof is ascorbic acid.

10. The composition of claim 1, wherein said non-fatty acid or salt thereof is selected from the group consisting of acetic acid, adipic acid, citric acid, formic acid, lactic acid, malic acid, folic acid, pantothenic acid, and biotin.

11. A stable liquid composition consisting essentially of:
   (a) chitosan, a non-fatty acid or salt thereof, and water or aqueous solution, wherein each are present in said composition in a stabilizing amount sufficient to effect the formation of a stable liquid composition, and
   (b) dietary fiber.

12. The composition of claim 11, wherein said dietary fiber is inulin.

13. The composition of claim 11, wherein said dietary fiber is present in an amount of from about 2.0% to about 10.0% (volume/volume) of said composition.

14. A stable liquid composition consisting essentially of:
   (a) chitosan, a non-fatty acid or salt thereof, and water or aqueous solution, wherein each are present in said composition in a stabilizing amount sufficient to effect the formation of a stable liquid composition; and
   (b) dietary fiber, preservative, and flavor.

15. The composition of claim 14, wherein said preservative is present in an amount of from about 2.5% to about 4.0% (mass/volume) of said composition.

16. The composition of claim 14, wherein said preservative is selected from the group consisting of sodium benzoate, potassium sorbate, benzoic acid, methylparaben, alcohol, and sorbic acid.

17. The composition of claim 14, wherein said flavor is present in an amount of from about 2.0% to about 4.0% (mass/volume) of said composition.

18. The composition of claim 14, which binds at least about 2 grams of fat per gram of chitosan.

19. A stable liquid composition consisting essentially of:
   (a) chitosan, a non-fatty acid or salt thereof, and water or aqueous solution, wherein each are present in said composition in a stabilizing amount sufficient to effect the formation of a stable liquid composition; and
   (b) dietary fiber, preservative, and flavor,
      wherein said chitosan is present in an amount of from about 2.5% to about 4.0% (mass/volurne),
      said non-fatty acid or salt thereof is present in an amount of from about 2.5% to about 4.0% (mass/volume),
      said dietary fiber is present in an amount of from about 2.0% to about 10.0% (volume/volume),
      said preservative is present in an amount of from about 2.5% to about 4.0% (mass/volume), and
      said flavor is present in an amount of from about 2.0% to about 4.0% (mass/volume) of said composition.

20. A method of preparing the composition of claim 1, said method comprising:
   (a) obtaining solid chitosan;
   (b) wetting said chitosan with water or aqueous solution; and
   (c) mixing a non-fatty acid or acid salt with said chitosan and said water or aqueous solution to obtain said composition.

21. A method of preparing the composition of claim 11, said method comprising:
   (a) obtaining solid chitosan;
   (b) wetting said chitosan with water or aqueous solution;
   (c) mixing a non-fatty acid or acid salt with said chitosan and said water or aqueous solution to obtain a chitosan-acid mixture;
   (d) in a separate vessel, adding water or aqueous solution;
   (e) mixing dietary fiber with said water or aqueous solution in said separate vessel; and
   (f) mixing said chitosan-acid mixture with the contents of said separate vessel to obtain said composition.

22. A method of preparing the composition of claim 14, said method comprising:
   (a) obtaining solid chitosan;
   (b) wetting said chitosan with water or aqueous solution;
   (c) mixing a non-fatty acid or acid salt with said chitosan and said water or aqueous solution to obtain a chitosan-acid mixture;
   (d) in a separate vessel, adding water or aqueous solution;
   (e) mixing preservative in said separate vessel;
   (f) mixing dietary fiber in said separate vessel;
   (g) mixing flavor in said separate vessel; and
   (h) mixing the contents of said separate vessel with said chitosan-acid mixture to obtain said composition.

23. A method of preparing the composition of claim 14, said method comprising:
   (a) obtaining solid chitosan;
   (b) wetting said chitosan with water or aqueous solution;
   (c) mixing a non-fatty acid or acid salt with said chitosan and said water or aqueous solution to obtain a chitosan-acid mixture;
   (d) in a separate vessel, adding water or aqueous solution;
   (e) mixing preservative in said separate vessel;
   (f) mixing the contents of said separate vessel with said chitosan-acid mixture to obtain a chitosan-acid-preservative mixture;

(g) mixing dietary fiber with said chitosan-acid-preservative mixture; and (h) mixing flavor with said chitosan-acid-preservative mixture to obtain said composition.

24. A method of using the composition of claim 1 in a subject's weight treatment program, said method comprising said subject's consumption of said composition comprising an effective fat binding amount of chitosan either prior to, concurrent with, or following a meal so as to result in weight treatment.

25. The method of claim 24, wherein said meal contains an item selected from the group consisting of fat, free fatty acids, cholesterol, sterols other than cholesterol, and bile acids.

26. In a method of weight treatment, the improvement comprising a subject's consumption of the composition of claim 1 comprising an effective fat binding amount of chitosan either prior to, concurrent with, or following a meal so as to result in weight treatment.

27. A method of using the composition of claim 1 in a subject's cholesterol treatment program, said method comprising said subject's consumption of said composition comprising an effective fat binding amount of chitosan either prior to, concurrent with, or following a meal so as to result in cholesterol treatment.

28. The method of claim 27, wherein said meal contains an item selected from the group consisting of cholesterol, sterols other than cholesterol, and bile acids.

29. In a method of cholesterol treatment, the improvement comprising a subject's consumption of the composition of claim 1 comprising an effective cholesterol binding amount of chitosan either prior to, concurrent with, or following a meal so as to result in cholesterol treatment.

30. A method of using the composition of claim 11 in a subject's weight treatment program, said method comprising said subject's consumption of said composition comprising an effective fat binding amount of chitosan either prior to, concurrent with, or following a meal so as to result in weight treatment.

31. The method of claim 30, wherein said meal contains an item selected from the group consisting of fat, free fatty acids, cholesterol, sterols other than cholesterol, and bile acids.

32. In a method of weight treatment, the improvement comprising a subject's consumption of the composition of claim 11 comprising an effective fat binding amount of chitosan either prior to, concurrent with, or following a meal so as to result in weight treatment.

33. A method of using the composition of claim 11 in a subject's cholesterol treatment program, said method comprising said subject's consumption of said composition comprising an effective cholesterol binding amount of chitosan either prior to, concurrent with, or following a meal so as to result in cholesterol treatment.

34. The method of claim 33, wherein said meal contains an item selected from the group consisting of cholesterol, sterols other than cholesterol, and bile acids.

35. In a method of cholesterol treatment, the improvement comprising a subject's consumption of the composition of claim 11 comprising an effective cholesterol binding amount of chitosan either prior to, concurrent with, or following a meal so as to result in cholesterol treatment.

36. A method of using the composition of claim 14 in a subject's weight treatment program, said method comprising said subject's consumption of said composition comprising an effective fat binding amount of chitosan either prior to, concurrent with, or following a meal so as to result in weight treatment.

37. The method of claim 36, wherein said meal contains an item selected from the group consisting of fatty free fat acids, cholesterol, sterols other than cholesterol, and bile acids.

38. In a method of weight treatment, the improvement comprising a subject's consumption of the composition of claim 14 comprising an effective fat binding amount of chitosan either prior to, concurrent with, or following a meal so as to result in weight treatment.

39. A method of using the composition of claim 14 in a subject's cholesterol treatment program, said method comprising said subject's consumption of said composition comprising an effective cholesterol binding amount of chitosan either prior to, concurrent with, or following a meal so as to result in cholesterol treatment.

40. The method of claim 39, wherein said meal contains an item selected from the group consisting of cholesterol, sterols other than cholesterol, and bile acids.

41. In a method of cholesterol treatment, the improvement comprising a subject's consumption of the composition of claim 14 comprising an effective cholesterol binding amount of chitosan either prior to, concurrent with, or following a meal so as to result in cholesterol treatment.

42. A method of reducing absorption of lipids and triglycerides into a blood stream of a subject, the method comprising consuming the composition comprising an effective lipids and triglycerides binding amount of chitosan according to claim 1, to reduce the absorption of said lipids and triglycerides into the blood stream of said subject, either prior to, concurrent with, or following a meal.

43. A method of reducing absorption of lipids and triglycerides into a blood stream of a subject, the method comprising consuming the composition comprising an effective lipids and triglycerides binding amount of chitosan according to claim 11, to reduce the absorption of said lipids and triglycerides into the blood stream of said subject, either prior to, concurrent with, or following a meal.

44. A method of reducing absorption of lipids and triglycerides into a blood stream of a subject, the method comprising consuming the composition comprising an effective lipids and triglycerides binding amount of chitosan according to claim 14, to reduce the absorption of said lipids and triglycerides into the blood stream of said subject, either prior to, concurrent with, or following a meal.

\* \* \* \* \*